US008768424B2

(12) United States Patent
Crowe et al.

(10) Patent No.: US 8,768,424 B2
(45) Date of Patent: Jul. 1, 2014

(54) PHOTOPLETHYSMOGRAPHY

(75) Inventors: John Crowe, University Park (GB); Mark Grubb, University Park (GB); Barrie Hayes-Gill, University Park (GB); Nicholas Miles, University Park (GB)

(73) Assignee: The University of Nottingham (GB)

( * ) Notice: Subject to any disclaimer, the term of this patent is extended or adjusted under 35 U.S.C. 154(b) by 1278 days.

(21) Appl. No.: 12/296,513

(22) PCT Filed: Apr. 11, 2007

(86) PCT No.: PCT/GB2007/001355
§ 371 (c)(1),
(2), (4) Date: Apr. 2, 2009

(87) PCT Pub. No.: WO2007/122375
PCT Pub. Date: Nov. 1, 2007

(65) Prior Publication Data
US 2009/0306487 A1    Dec. 10, 2009

(30) Foreign Application Priority Data
Apr. 11, 2006   (GB) .................................. 0607270.6

(51) Int. Cl.
*A61B 5/00*   (2006.01)
(52) U.S. Cl.
USPC ........................................................ 600/322
(58) Field of Classification Search
USPC ......... 600/322–324, 326, 328, 330, 331, 336, 600/476
See application file for complete search history.

(56) References Cited

U.S. PATENT DOCUMENTS

| 4,258,719 A | 3/1981 | Lewyn |
| 4,989,169 A | 1/1991 | McCaslin et al. |

(Continued)

FOREIGN PATENT DOCUMENTS

| EP | 0314324 A1 | 5/1989 |
| EP | 0335357 A2 | 10/1989 |

(Continued)

OTHER PUBLICATIONS

Ramanujam et al. "Sources of Phase Noise in Homodyne and Heterodyne Phase Modulation Devices used for Tissue Oximetry Studies", Review of Scientific Instruments Aug. 1998, vol. 69, No. 8, p. 3042-3054.
Branche et al. "Measurrment Reproducibility and Sensor Placement Considerations in Designing a Wearable Pulse Oximeter for Military Applications", IEEE 2004, p. 216-217.

(Continued)

*Primary Examiner* — Brian Szmal
*Assistant Examiner* — Megan Leedy
(74) *Attorney, Agent, or Firm* — Brooks Kushman P.C.

(57) ABSTRACT

A photoplethysmograph device includes a light source for illuminating a target object. A modulator drives the light source such that the output intensity varies as a function of a modulation signal at a modulation frequency. A detector receives light from the target object and generates an electrical output as a function of the intensity of received light. A demodulator with a local oscillator receives the detector output and produces a demodulated output, insensitive to any phase difference between the modulation signal and the oscillator, indicative of blood volume as a function of time and/or blood composition. A number of demodulators may be provided to derive signals from multiple light sources of different wavelengths, or from an array of detectors. The plethysmograph may operate in a transmission mode or a reflectance mode. When in a reflectance mode, the device may use the green part of the optical spectrum and may use polarizing filters.

15 Claims, 15 Drawing Sheets

(56) References Cited

U.S. PATENT DOCUMENTS

| | | | |
|---|---|---|---|
| 7,890,158 B2* | 2/2011 | Rowe et al. | 600/476 |
| 2003/0229276 A1* | 12/2003 | Sarussi et al. | 600/322 |
| 2005/0197583 A1* | 9/2005 | Chance | 600/476 |

FOREIGN PATENT DOCUMENTS

| | | | |
|---|---|---|---|
| WO | 9822018 A1 | 5/1998 | |
| WO | 9846125 A1 | 10/1998 | |
| WO | 9940841 A1 | 8/1999 | |
| WO | 9952420 A1 | 10/1999 | |
| WO | 0144780 A2 | 6/2001 | |

OTHER PUBLICATIONS

Hayes et al. "Artifact reduction in photoplethysmography", Applied Optics Nov. 1, 1998, vol. 37, No. 31, p. 7437-7446.

Cui et al. "In Vivo Reflectance of Blood and Tissue as a Function of Light Wavelength", IEEE Transactions on Biomedical Engineering Jun. 1990, vol. 37, No. 6, p. 632-639.

International Search Report for PCT/GB2007/001355, Completed by the European Patent Office on Mar. 13, 2008, 5 Pages.

R. Xue, A New Method of an IF I/O Demodulator for Narrowband Signals, Conference Proceedings/ IEEE International Symposium on Circuits and Systems (ISCAS): May 23-26, 2005, International Conference Center, Kobe, Japan, IEEE Service Center, Piscataway, NJ, May 23, 2005, pp. 3817-3820, XP010816497, DOI: 10.1109/ISCAS.2005.1465462 ISBN: 978-0-7803-8834-5.

\* cited by examiner

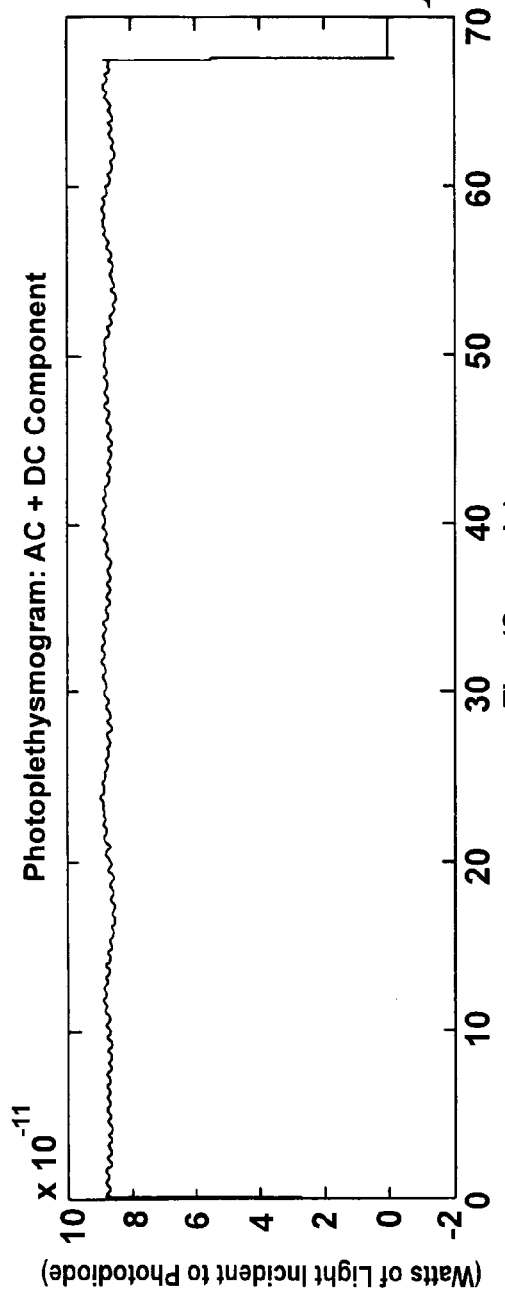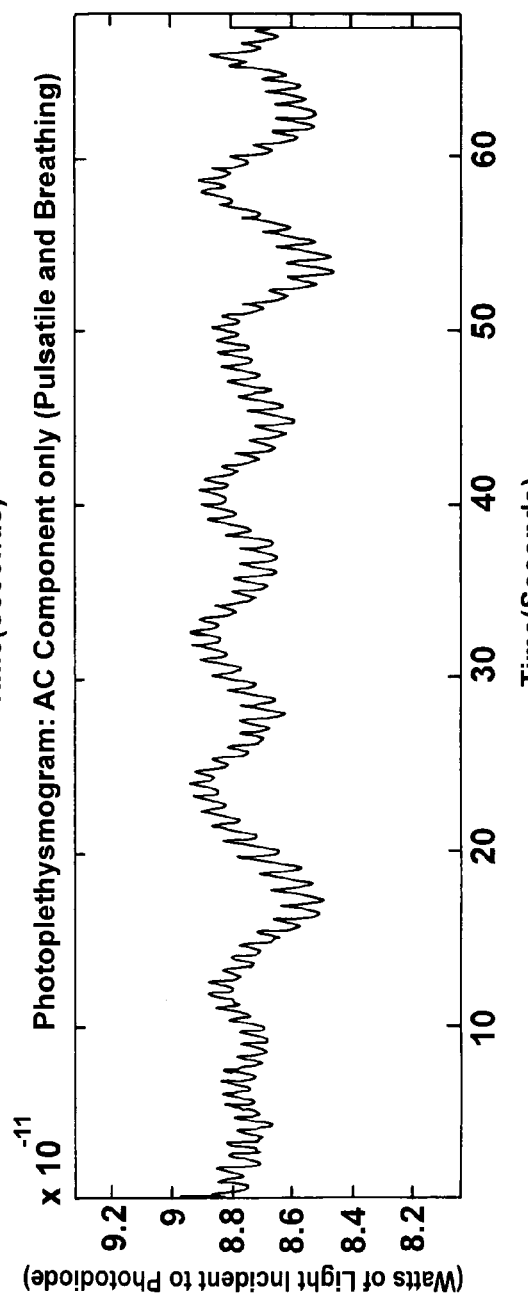

PHOTOPLETHYSMOGRAPHY

The present invention relates photoplethysmography and in particular to a method and apparatus for measuring pulse rate, breathing rate and blood constituents in the human or animal body.

The word plethysmography is a combination of the Greek words Plethysmos, meaning increase, and graph, meaning write. A plethysmograph is an instrument, method or apparatus used to measure the variations in blood volume in the body. Photoplethysmography (hereinafter also referred to as 'PPG') refers to the use of light to measure these changes in volume, and therefore a photoplethysmograph is an instrument, method or apparatus that uses light to perform these measurements.

Although the human or animal body is generally assumed to be opaque to light, most soft tissue will transmit and reflect both visible and near-infrared radiation. Therefore, if light is projected onto an area of skin and the emergent light is detected after its interaction with the skin, blood and other tissue, time varying changes of light intensity having a relation with blood volume, known as the plethysmogram, can be observed. This time varying light intensity signal will depend on a number of factors including the optical properties of the tissues and blood at the measurement site, and the wavelength of the light source. The signal results because blood absorbs light and the amount of light absorbed, and hence the intensity of remaining light detected, varies in relation with the volume of blood illuminated. Variation in the plethysmogram is caused by the variation in blood volume flowing in the tissue.

This technique was introduced in 1937 by Hertzman. He was the first to use the term photoplethysmography and suggested that the resultant plethysmogram represented volumetric changes of blood in the skin's vessels.

The plethysmogram is usually described with respect to its AC and DC components. The absorption of light by non-pulsatile blood, bone and tissue is assumed to be constant and gives rise to the DC component. The DC component represents the volume of non-pulsatile blood below the sensor, plus light reflected and scattered off the skin, bone and other tissues. The AC component is caused by the time varying absorption of light caused by temporal changes in blood volume below the sensor.

Changes in the blood volume can be caused by cardiovascular regulation, blood pressure regulation, thermoregulation and respiration. Thus the plethysmogram can be analysed to determine information on such parameters as pulse rate, breathing rate, blood pressure, perfusion, cardiac stroke volume and respiratory tidal volume. These can be observed as periodic and non-periodic changes in the amplitude of AC and DC components in the plethysmogram. This has been described in more detail in Kamal et al: 'Skin Photoplethysmography—a review', Computer Methods and Programs in Biomedicine, 28 (1989) 257-269). The plethysmogram can also be analysed to determine blood constituents. One such technique is pulse oximetry, which determines the relative amount of oxygen in the blood. Other blood constituents can also be measured by using photoplethysmography.

There are two modes of photoplethysmography, the transmission mode and the reflection mode. In transmission mode the light source is on one side of the tissue and the photodetector is placed on the other side, opposite the light source. The use of transmission mode is limited to areas where the tissue is thin enough to allow light to propagate, for example the fingers, toes and earlobes of a human subject.

In reflection mode the light source and photodetector are place side-by-side. Light entering the tissue is reflected and a proportion of this is detected at the photodetector. This source-detector configuration is more versatile and allows measurements to be performed on almost any area of tissue. However, the use of reflectance mode is much harder to design than transmission because the signal level is significantly lower at the most effective wavelengths. Thus, considerable attention must be given to maximising signal-to-noise ratio. As a result, the most common PPG sensors use transmission mode and hence are restricted to positions where light can pass through tissue.

As a photodetector is used to measure light from the source, the photoplethysmograph can also respond to interfering signals from other sources of light, for example fluorescent lighting and computer monitors. The sensor must also respond to changes in the light propagating through tissue, i.e. the plethysmogram. These physiological changes contain frequency components between DC and 25 Hz. However, it is desirable for the sensor not to respond to ambient light noise. Accordingly, the photoplethysmograph should reject ambient light noise while detecting the plethysmogram in the bandwidth of interest.

A second source of interference is other electrical apparatus. Other electrical devices can generate radio frequency signals that a photoplethysmograph can detect. It is desirable to minimise the sensitivity of the system to interfering sources of this nature.

A third source of interference is the electrical noise generated by the photoplethysmograph itself. Such noise can be generated by electronic components, and can include thermal noise, flicker noise, shot noise, as well as noise spikes, for example, harmonics generated by missing codes in an analogue-to-digital converter. It is also desirable to minimise the sensitivity of the system to interference from these sources.

A known technique for reducing the noise generated by these three sources of interference is to drive the sensor's light source with a carrier modulated at a frequency that is not present, or dominant, in the ambient light, electrical radio frequency signals, or photoplethysmograph system noise. This can be done by modulating the sensor's light source with a square wave, by pulsing it on and off. The detected signals are then band pass filtered to attenuate interference outside the frequency range of interest. Subsequent demodulation will recover the plethysmogram. In general, any periodic signal such as a sine wave may be used to modulate the light source.

Though modulated light photoplethysmography exists in the prior art, there are still critical limitations in how it has been applied, especially in terms of suitable signal conditioning circuits for attenuating or removing noise, and demodulation. For example, EP0335357, EP0314324, WO0144780 and WO9846125 disclose modulated light photoplethysmography. However, they use a demodulation method and apparatus that requires the modulating and demodulating carrier phase to be synchronised. Error in the synchronisation timing will add noise to the demodulated signal (timing jitter or phase noise). The prior art also fails to make full use of band pass filter characteristics to remove ambient interfering light, by still relying on a separate channel to measure ambient light, and later subtracting it from the signal, which adds further complexity and is arguably less efficient at attenuating interference. These limitations reduce immunity to broadband and narrowband noise from sources such as fluorescent lighting, computer monitors, sunlight, incandescent light, electrical RF interference, thermal noise, flicker noise, and shot noise.

A further limitation in the prior art is the choice of wavelength for reflectance mode sensors. Both reflection mode and transmission mode sensors use light sources in the red and/or infrared part of the spectrum, wavelengths between 600 nm and 1000 nm being typical. However, red/infrared reflectance sensors do not function well because light at red and infrared wavelengths is poorly absorbed by blood. This results in low modulation of the reflected signal and therefore a small AC component. Therefore red/infrared reflectance probes give poor results when compared to transmittance probes. It has been shown in Weija Cui et al: "*In Vivo Reflectance of Blood and Tissue as a Function of Light Wavelength*", IEEE Transactions on Biomedical Engineering, Volume 37, No 6, June 1996), that a larger plethysmogram AC component amplitude can be recorded if a reflectance mode sensor uses light of wavelengths between 500 nm and 600 nm (green light).

A continuous non-modulated green light photoplethysmograph was described in WO 9822018A1. However, the objective of this invention was reflectance pulse oximetry, and the patent does not explain the steps necessary to produce a reliable photoplethysmograph suitable for measuring the plethysmogram AC and DC component. Such a green light sensor would be necessary to reliably detect the AC component, for example heart rate, but moreover the breathing signal, which is extremely small and was not detected by this system.

In Benten et al: "*Integrated synchronous receiver channel for optical instrumentation applications*" Proceedings of SPIE—The International Society for Optical Engineering, Volume 3100, 75-88, 1997), a modulated light reflectance photoplethysmograph is described that uses a switching multiplier to systematically change the gain of the signal path between +1 and −1. This is the equivalent of mixing the modulated signal with a square wave to recover the plethysmogram. However, similar to the other prior art described previously, this method needs the modulating carrier and demodulating local oscillator signals to be in-phase.

It is an object of the present invention to provide an improved plethysmograph.

According to one aspect, the present invention provides a photoplethysmograph device comprising:
- a light source for illuminating a target object;
- a modulator for driving the light source such that the output intensity varies as a function of a modulation signal at a modulation frequency;
- a detector for receiving light from the target object and generating an electrical output as a function of the intensity of received light;
- a demodulator for receiving the detector output, having a local oscillator and producing a demodulated output representative of the modulation signal and any sidebands thereof, in which the demodulator is insensitive to any phase difference between the modulation signal and the oscillator of the demodulator; and
- means for generating, from the demodulated output, a signal indicative of blood volume as a function of time and/or blood composition.

According to another aspect, the present invention provides a method of generating a plethysmogram, comprising the steps of:
- illuminating a target object with a light source;
- driving the light source with a modulator such that the output intensity varies as a function of a modulation signal at a modulation frequency;
- receiving light from the target object with a detector and generating an electrical output as a function of the intensity of received light;
- receiving the detector output in a demodulator having a local oscillator and producing a demodulated output representative of the modulation signal and any sidebands thereof, in which the demodulator is insensitive to any phase difference between the modulation signal and the oscillator of the demodulator; and
- generating, from the demodulated output, a signal indicative of blood volume as a function of time and/or blood composition.

According to another aspect, the present invention provides a photoplethysmograph device comprising:
- one or more light sources each for illuminating a portion of a target object;
- one or more modulators for driving the light sources such that the output intensity of each light source varies as a function of a modulation signal at a modulation frequency;
- one or more detectors for receiving light from the target object and generating one or more electrical outputs as a function of the intensity of received light;
- a plurality of demodulators each for receiving one or more of the electrical outputs and producing a demodulated output representative of the modulation signal of one of the modulated light sources and any sidebands thereof, to thereby produce a plurality of demodulated outputs corresponding to the plurality of light sources and/or plurality of detectors; and
- means for generating, from the demodulated outputs, plethysmogram signals indicative of blood volume as a function of time and/or blood composition for each of the demodulator outputs.

According to another aspect, the present invention provides a method of generating a plethysmogram, comprising the steps of:
- illuminating a portion of a target object with one or more light sources;
- driving the light sources with one or more modulators such that the output intensity of each light source varies as a function of a modulation signal at a modulation frequency;
- receiving light from the target object with one or more detectors and generating one or more electrical outputs as a function of the intensity of received light;
- receiving one or more of the electrical outputs with a plurality of demodulators, each producing a demodulated output representative of the modulation signal of one of the modulated light sources and any sidebands thereof, to thereby produce a plurality of demodulated outputs corresponding to the plurality of light sources; and
- generating, from the demodulated outputs, plethysmogram signals indicative of blood volume as a function of time and/or blood composition for each of the demodulator outputs of the pixel array.

According to another aspect, the present invention provides a photoplethysmograph device for non-contact use, comprising:
- a light source for illuminating a target object via a first polarising filter;
- a modulator for driving the light source such that the output intensity varies as a function of a modulation signal at a modulation frequency;
- a detector for receiving light from the target object via a second polarising filter having a different polarisation state than the first polarising filter, the detector adapted to generate an electrical output as a function of the intensity of received light;
- a demodulator for receiving the detector output and producing a demodulated output representative of the modulation signal and any sidebands thereof; and means for generating, from the demodulated output, a signal indicative of blood volume as a function of time and/or blood composition.

According to another aspect, the present invention provides a method of generating a photoplethysmogram, comprising the steps of:
 illuminating a target object with a light source via a first polarising filter;
 driving the light source with a modulator such that the output intensity varies as a function of a modulation signal at a modulation frequency;
 receiving light from the target object with a detector via a second polarising filter having a different polarisation state than the first polarising filter, the detector generating an electrical output as a function of the intensity of received light;
 receiving the detector output with a demodulator and producing a demodulated output representative of the modulation signal and any sidebands thereof; and
 generating, from the demodulated output, a signal indicative of blood volume as a function of time and/or blood composition.

According to another aspect, the present invention provides a photoplethysmograph device for non-contact use, comprising:
 a light source for illuminating a target object with optical radiation of wavelength less than 600 nm;
 a modulator for driving the light source such that the output intensity varies as a function of a modulation signal at a modulation frequency;
 a detector for receiving light from the target object and adapted to generate an electrical output as a function of the intensity of received light, the light source and detector being disposed laterally adjacent to one another on a substrate such that the active surfaces thereof can be directed towards substantially the same point on a surface of the target body;
 a demodulator for receiving the detector output and producing a demodulated output representative of the modulation signal and any sidebands thereof; and
 means for generating, from the demodulated output, a signal indicative of blood volume as a function of time and/or blood composition.

According to another aspect, the present invention provides a method of generating a photoplethysmogram, comprising the steps of:
 illuminating a target object with optical radiation of wavelength less than 600 nm from a light source;
 driving the light source with a modulator such that the output intensity varies as a function of a modulation signal at a modulation frequency;
 receiving light from the target object with a detector to generate an electrical output as a function of the intensity of received light, the light source and detector being disposed laterally adjacent to one another on a substrate such that the active surfaces thereof can be directed towards substantially the same point on a surface of the target body;
 receiving the detector output with a demodulator and producing a demodulated output representative of the modulation signal and any sidebands thereof; and
 generating, from the demodulated output, a signal indicative of blood volume as a function of time and/or blood composition.

The invention provides a modulated light photoplethysmograph device. In selected embodiments, it combines the features of modulated light, band pass filtering, and IQ demodulation to give a plethysmogram of perfuse tissue. When used in reflectance mode, light in the blue and/or green portion of the optical spectrum is used which gives a larger pulsatile signal and improved signal to noise ratio.

Selected embodiments of the invention provide improved reliability through the reduction of noise when the photoplethysmograph device is used in transmission mode. In addition, the choice of light in the blue/green portion of the optical spectrum (i.e. wavelengths of between 400 nm and 600 nm) gives improved reliability through the reduction of noise and the increase in AC component signal amplitude, when the photoplethysmograph device is used in reflection mode.

Selected embodiments can be applied to different photolethysmography techniques including single wavelength photoplethysmography, multiple wavelength photoplethysmography, pixel array photoplethysmography, and non-contact photoplethysmography.

Embodiments of the present invention will now be described by way of example and with reference to the accompanying drawings in which:

FIG. 13a is a photoplethysmogram showing a combined AC and DC output of a photoplethysmograph device;

FIG. 13b is a photoplethysmogram showing the magnified AC component from FIG. 13a;

SINGLE WAVELENGTH PHOTOPLETHYSMOGRAPH DEVICE

Figure 1:
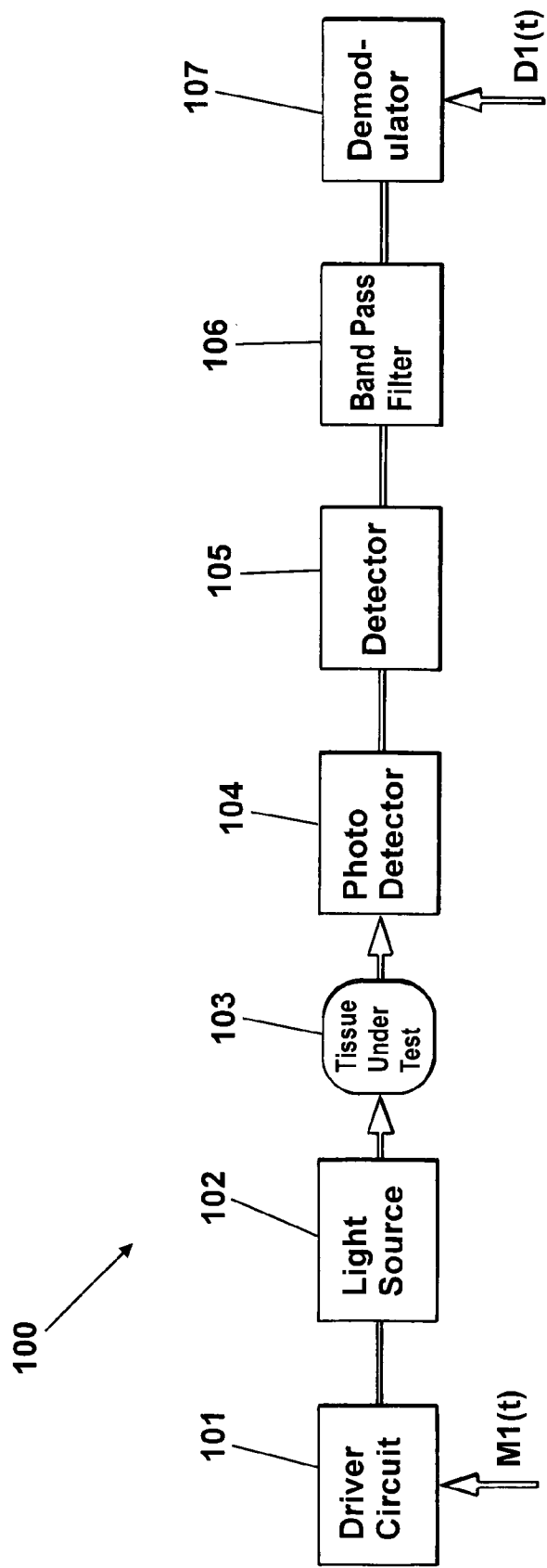
FIG. 1 is a functional block diagram of a single wavelength photoplethysmograph device.

With reference to FIG. 1, a photoplethysmograph device 100 comprises a driver circuit 101 which is coupled to energise a light source 102 with modulated drive signal such that the output intensity of the light source varies as a function of a modulation signal having a specific modulation frequency ($f_m$) and modulation amplitude (M1($t$)). The waveform driving the light source is therefore a modulating carrier characterised by its frequency and amplitude.

The light source 102 is configured to illuminate a target object 103 such as an area of tissue of the human or animal body. The light source 102 preferably comprises one or more light emitting devices each of a given wavelength or range of wavelengths.

A photodetector 104 is configured to receive light from the target object 103 after its interaction therewith. Depending on the relative positioning of the light source 102, the target object 103 and the photodetector 104, this received light may be one or more of light that has been transmitted through the target object, light that has been reflected from the surface of the target object, and light that has been scattered by and/or reflected from structures or fluids within the target object. The photodetector will generate an electrical current that is a function of, e.g. proportional to, the amount of light incident to its active area.

A detector 105 may be provided to convert the electrical current from the photodetector 104 to a voltage that is proportional to the current. The detector 105 may incorporate an amplifier (not shown). The gain of that amplifier can be rolled off at a frequency greater than the modulation frequency. The detector 105 and amplifier can, with careful design, minimise the noise at the input to a band pass filter 106 coupled thereto. In a general sense, the photodetector 104 and detector 105 functions may be provided by any detector capable of receiving light from the target object and generating an electrical output that is a function of the intensity of the received light.

The band pass filter 106 may be provided for attenuating signals outside a bandwidth of interest. The filter bandwidth is preferably centred on the modulation frequency $f_m$ and is sufficiently wide to pass the modulating carrier and sidebands caused by plethysmogram amplitude modulation, but narrow enough to attenuate frequency components of interference and noise. To reduce noise, the bandwidth of the band pass filter 106 should be as narrow as possible. It need only be wide enough to pass the upper and lower sidebands of the plethysmogram, typically but not limited to 50 Hz. The band pass filter 106 may incorporate an amplifier (not shown) to provide additional gain. The band pass filter 106 and amplifier are preferably designed to minimise noise at the input of the following stage, namely a demodulator 107. It will be appreciated that the provision of a band pass filter 106 is not always necessary but, if employed, an increase in signal-to-noise ratio (SNR) may result.

Figure 2:
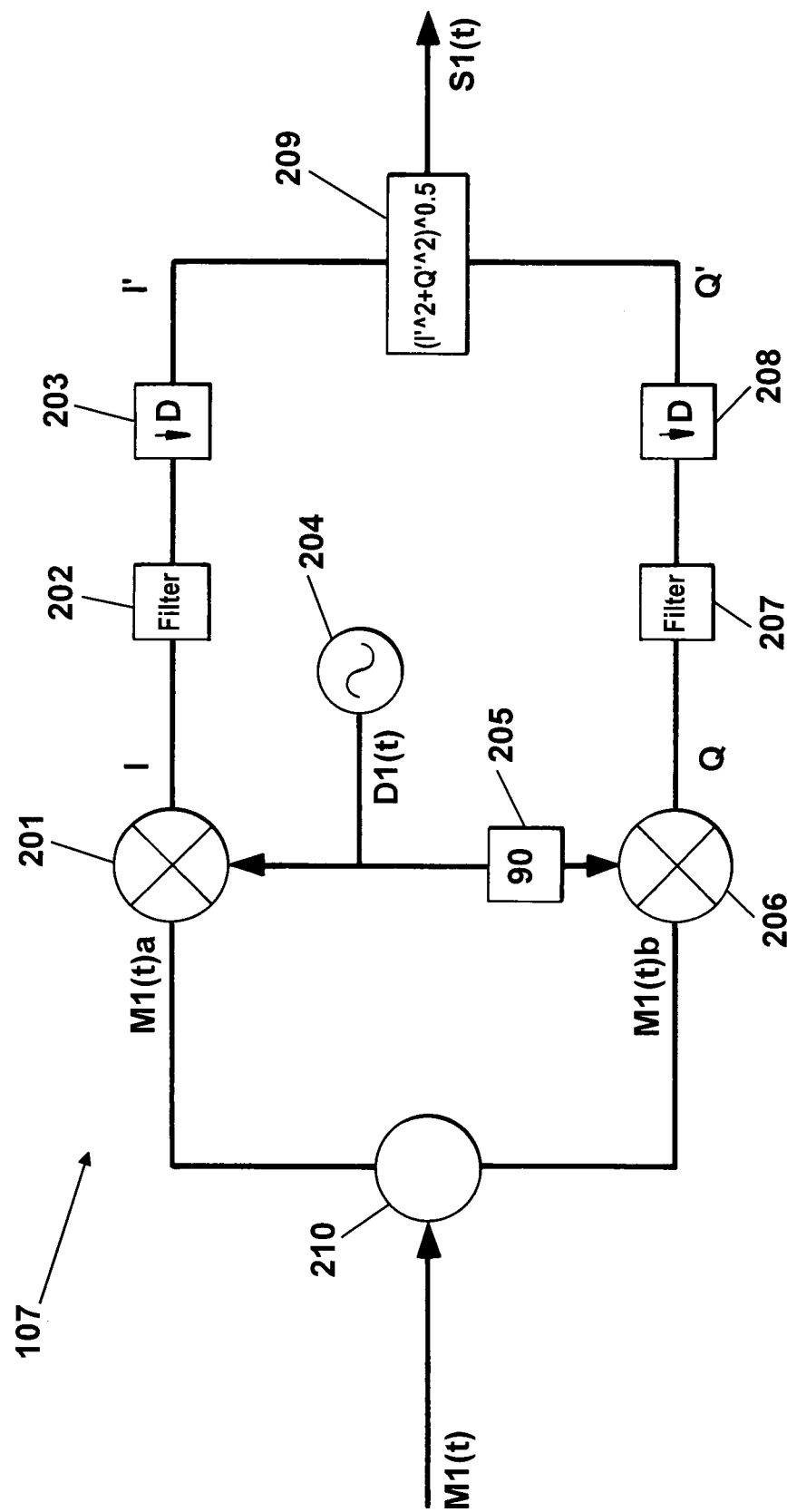
FIG. 2 is a functional block diagram of a demodulator suitable for use in the photoplethysmograph device of FIG. 1.

A preferred arrangement of demodulator 107 is shown in more detail in FIG. 2. The demodulator 107 is adapted to demodulate the output of the band pass filter 106 and hence recover a plethysmogram from the detected light received from the target object. The preferred demodulator 107 uses a method that is insensitive to the phase difference between the modulation carrier and a demodulation carrier. In other words, the demodulator is insensitive to any phase difference between the modulation signal and an oscillator in the demodulator, as will be explained later. Thus, it is unnecessary to maintain a predetermined phase relationship between the modulation and demodulation process.

The demodulator 107 may comprise a multiplexer 210 for splitting the modulated signal M1($t$) into two channels. A first channel processes a first modulated input signal M1($t$)a and a second channel processes a second modulated input signal M1($t$)b. The first modulated input signal M1($t$)a is provided as input to a first multiplier 201 together with an output of a first demodulator local oscillator (LO) signal 204, D1($t$). The frequency of the local oscillator signal 204 is preferably substantially equal to the frequency of the modulation signal and therefore equal to the modulating carrier frequency of input signal M1($t$). The result of the multiplication of M1($t$)a with the first LO signal 204 is an I ('in phase') signal. In the second channel, the second modulated input signal is multiplied, using a multiplier 206, with a second demodulator local oscillator (LO) signal that also has a frequency preferably substantially equal to the frequency of the modulation signal. However, the second demodulator LO signal is phase shifted by phase shifter 205 with respect to the first demodulator LO signal. The phase difference between the first demodulator LO and second demodulator LO is preferably 90 degrees. The result of the multiplication of M1($t$)b with the second demodulator LO signal is the Q ('quadrature phase') signal. It will be understood that the local oscillator, although shown as a producing a sine wave output, could produce other waveforms of the required frequency.

The separate I and Q signals are preferably separately low pass filtered in filter elements 202 and 207 respectively to remove unwanted harmonics and products of the multiplication process. Optionally, the resulting signals may be decimated in decimators 203 and 208 respectively to reduce the sample rate. The results of this are the I' and Q' signals.

The I' and Q' signals can be demultiplexed back into one signal at mixer 209 to provide the demodulated plethysmogram S1($t$). The demultixplexing process can include an algorithm or circuit that determines the square root of the sum of the squares of the I' and Q' signals.

Figure 18:
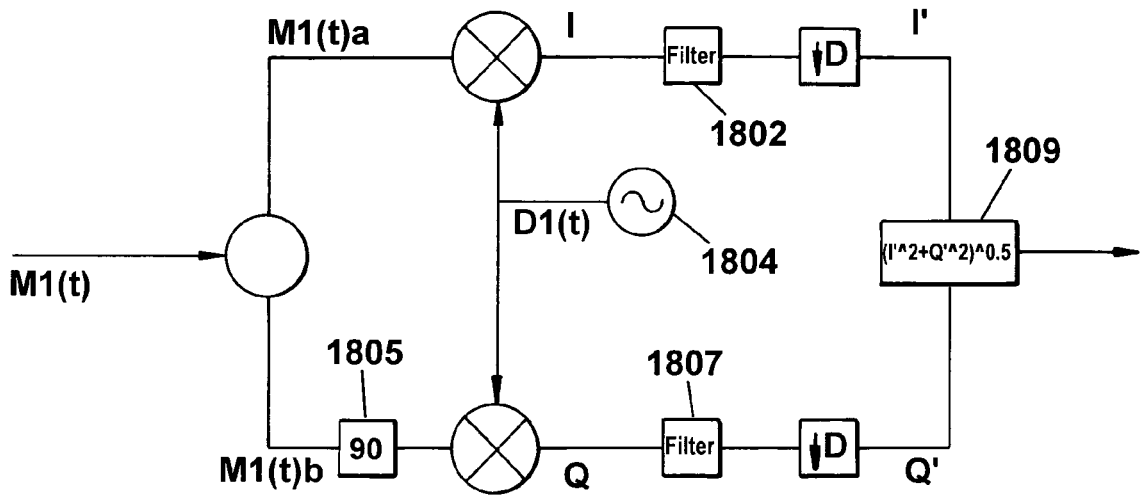
FIG. 18 is a functional block diagram of an alternative demodulator suitable for use in the photoplethysmograph device of FIG. 1.
Figure 19:
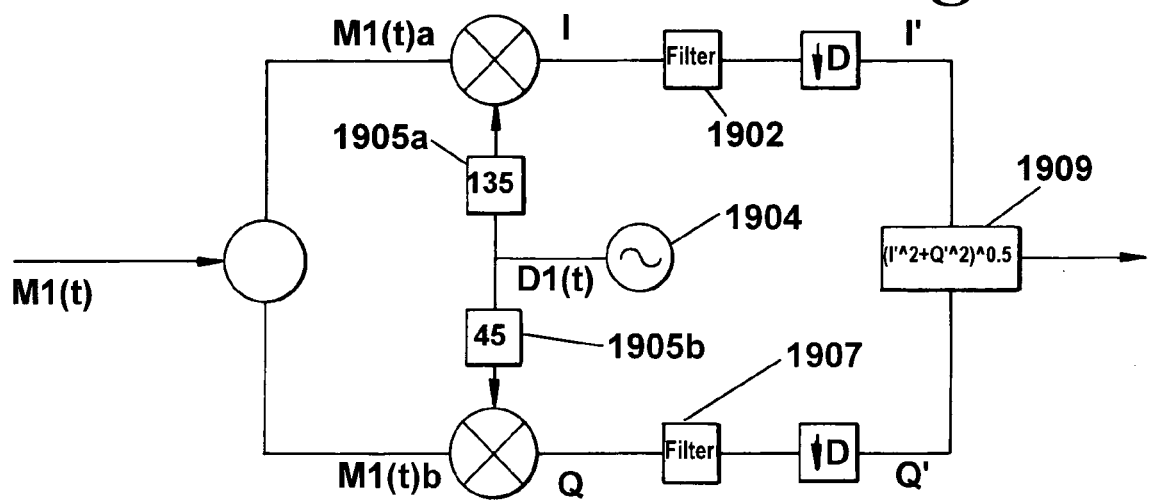
FIG. 19 is a functional block diagram of an alternative demodulator suitable for use in the photoplethysmograph device of FIG. 1.
Figure 20:
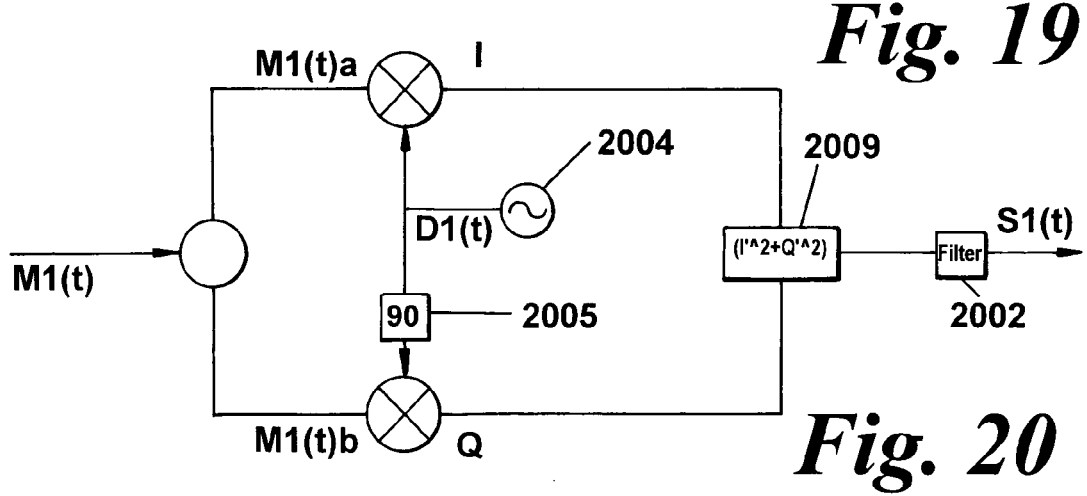
FIG. 20 is a functional block diagram of an alternative demodulator suitable for use in the photoplethysmograph device of FIG. 1.

The demodulator arrangement of FIG. 2 can be modified while still providing a demodulator that is insensitive to any phase difference between the modulation signal and the oscillator in the demodulator. FIGS. 18 to 20 show alternative arrangements each providing two channels in which, in the first channel the detector output is mixed with a local oscillator having a first phase relationship with the detector output and in the second channel the detector output is mixed with a local oscillator having a second phase relationship with the detector output. As in FIG. 2, the first and second phase relationships are preferably 90 degrees apart.

From inspection of the figures, it will be seen that this can be achieved by using a common local oscillator 204, 1804, 1904, 2004 that feeds the two channels with a different relative phase shift element 205, 1905a, 1905b, 2005 (FIGS. 2, 19 and 20) or by using a common local oscillator but a phase delay element 1805 (FIG. 18) provided in one or both channels to delay one or both of the signals M1($t$)a and M1($t$)b and thereby create a relative phase shift between them. FIG. 20 also illustrates that the filtering otherwise carried out by elements 202, 207 (or 1802, 1807, 1902, 1907) can alternatively be carried out after the mixer 209, 1809, 1909, 2009 by a filter 2002. Similarly, decimation can also be carried out after the mixer 209, 1809, 1909, 2009.

A means of detecting and attenuating harmonically related narrow band noise may be provided. This means can be adaptive so that changes in interference characteristics can be detected and filtering (or other means of rejection) adapted to maintain signal-to-noise ratio.

Figure 12:
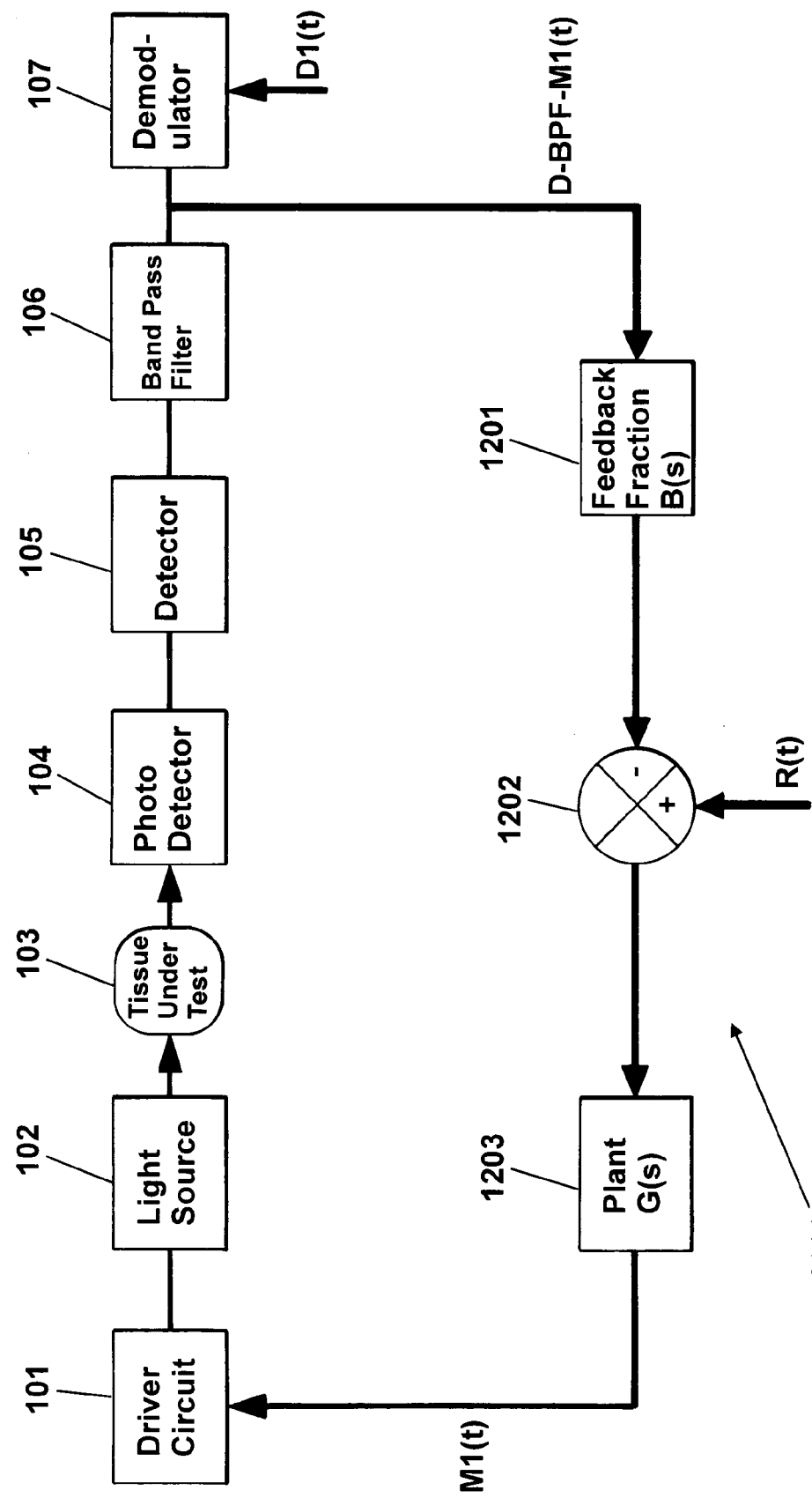
FIG. 12 is a functional block diagram of a light source brightness control loop suitable for use in the photoplethysmograph devices described herein.

A means of closed loop control can be provided to maintain the light source 102 at a brightness sufficient to detect the plethysmogram. A functional block diagram of this control loop 1200 is shown in FIG. 12. Similar elements to that shown in FIG. 1 are given corresponding reference numerals. The amplitude of the detected, band pass filtered, modulation carrier D-BPF-M1(t) can be measured and processed by a signal conditioning circuit 1201 in the feedback path, then compared with a reference value or range of values in comparator 1202. An error signal can then be generated and processed by a signal conditioning circuit or algorithm 1203 in the forward path. By using this technique, the amplitude of the waveform generated by the driver circuit can be adjusted to ensure the detected carrier amplitude falls within the given range, or near the reference. This will ensure, for example, that if too much light is received from the target object, the detector does not saturate, or if too little light is received from the target object 103, the plethysmogram does not go undetected. Thus, in a general aspect, the feedback control loop 1200 provides an example of a means for maintaining the output intensity of the light source 102 as a function of the detector output and at a level adequate to maintain detection of a plethysmogram from the demodulated output S1(t).

Multiple Wavelength Photoplethysmography

Figure 3:
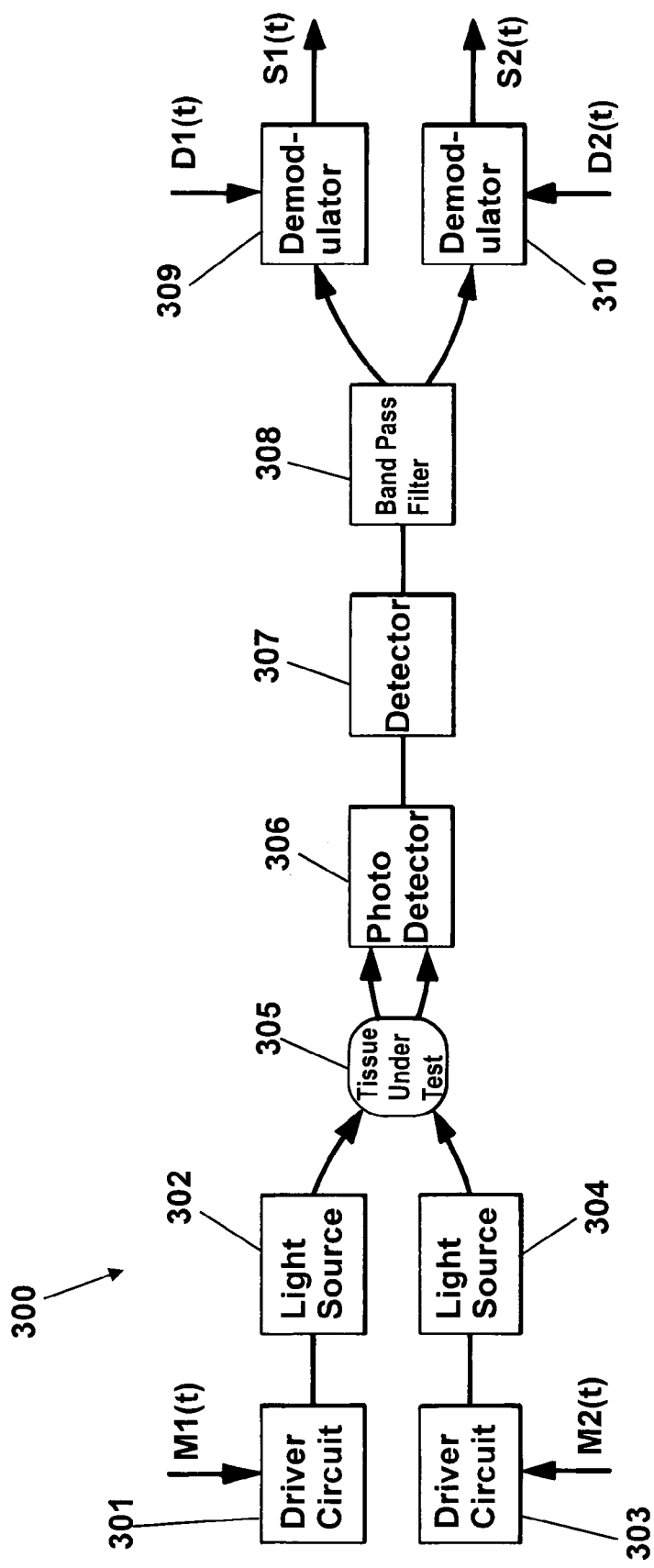
FIG. 3 is a functional block diagram of a multiple wavelength photoplethysmograph device.

FIG. 3 illustrates a photoplethysmograph device 300 that includes two or more light sources 302, 304 for emitting light at two or more different wavelengths into the target object (e.g. a tissue under test). An optical detector 306 is adapted to detect the light received from the target object, e.g. transmitted through the target object when the photoplethysmograph device is in transmission mode or reflected from the target object when the photoplethysmograph device is used in reflection mode. Driver circuits 301, 303 respectively are provided to energise the light sources 302, 304 each with a modulated drive signal having a modulation at a selected frequency and amplitude M1(t) and M2(t). Only two drivers and light sources are illustrated but it will be understood that generally a plurality of drivers and light sources can be used. Each light source can consist of one or more optical emitters that emit light at a single, given wavelength or range of wavelengths. The waveform of each light source can have a frequency different from those used to energise the other light sources. This waveform is the modulating carrier and is characterised by its frequency and amplitude. Each light source can optionally have a separate associated driver circuit. Each light source can optionally have a different wavelength.

A photodetector 306 is provided to detect light after its interaction with the target object 305 (e.g. tissue of a human or animal body). The photodetector 306 will generate a current proportional to the amount of light incident to its active area.

A detector 307 may be provided to convert the current from the photodetector 306 to a voltage that is proportional to the current. The detector 307 can incorporate an amplifier (not shown). The gain of that amplifier can be rolled-off at a frequency greater than the highest modulation frequency. The detector and amplifier can, with careful design, minimise the noise at the input to a band pass filter 308 and hence maximise the signal-to-noise ratio.

The band pass filter 308 may be provided for attenuating signals outside a bandwidth of interest. The filter bandwidth is preferably chosen so that the filter's lower roll-off is below the lowest modulating carrier frequency and the filter's upper roll-off is above the highest modulating carrier frequency. The bandwidth between the highest and lowest modulating carrier frequencies and the filter roll-off should be sufficiently wide to pass the modulating carrier and sidebands caused by plethysmogram amplitude modulation, but narrow enough to attenuate frequency components of interference and noise. To reduce noise the filter bandwidth should be as narrow as possible. It need only have sufficient range to pass the upper sideband of the highest modulation carrier and the lower sideband of the lowest modulation carrier. Typically 25 Hz above the highest modulating carrier frequency to 25 Hz below the lowest modulating carrier frequency is adequate. The band pass filter can incorporate an amplifier (not shown), which would provide additional gain. The band pass filter and amplifier can be designed to minimise noise at the input of the following stage. Filters can be included that provide a frequency response with a null or large attenuation at multiples of a fundamental frequency, for example a comb or moving average filter. These filters can be designed to attenuate the fundamental and harmonics of an interfering source.

Multiple demodulators 309 and 310 are provided for demodulating the output of the band pass filter to recover the plethysmogram at each modulating carrier frequency or at each wavelength of light. Preferably, the demodulators use a method of demodulation that is insensitive to the phase difference between each the modulating carrier and demodulating local oscillator, such as that described in connection with FIG. 2. Therefore, as previously stated, it is unnecessary to maintain a predetermined phase relationship between the modulation and demodulation process.

In this case, each demodulator will have a local oscillator D1(t) and D2(t) that preferably have the same frequency as the corresponding modulating carrier M1(t) and M2(t) respectively.

The output of this multiple wavelength photoplethysmograph device is multiple plethysmograms S1(t) and S2(t). Each is the plethysmogram for a given wavelength of light used to test the tissue. It will be understood that though the multi wavelength photoplethysmograph has been described with an example of two wavelengths, one wavelength provided by light source 302 and the second wavelength provided by light source 303, the invention can be modified to use more than two wavelengths by adding additional drivers, light sources and demodulators. These modulated multiple wavelengths not only allow selection of optical wavelengths for optimum SNR for the detection of pulse and breathing rate but also allow ratiometric measurements to be carried out to determine blood constituents. Thus, in a general aspect, the photoplethysmograph device may provide a means for automatically selecting one of the demodulated outputs S1(t), S2(t) that provides the best SNR for the data to be extracted from the plethysmogram.

As described above in connection with FIG. 12, closed loop control can also be used to maintain each light source at a given brightness.

Pixel Array Photoplethysmography

A combination of photodetector, detector, band pass filter and demodulator may be used to form one pixel of a multi-pixel photoplethysmograph imaging apparatus. Such an array can be produced as a microchip with the pixel and analogue or digital signal processing performed on chip.

Figure 4:
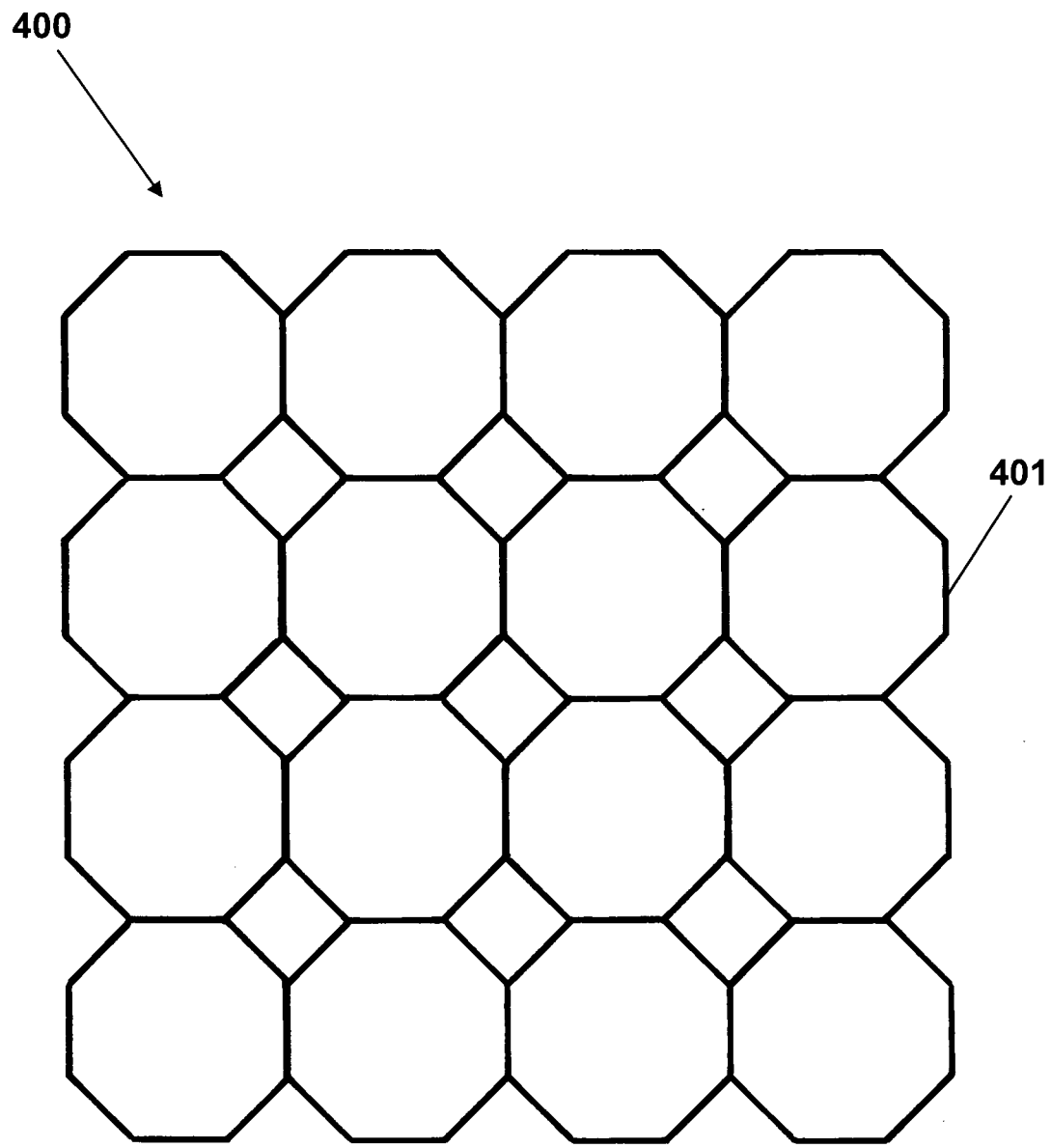
FIG. 4 is a schematic plan view of a pixel array photoplethysmograph device.

FIG. 4 shows a schematic plan view of a small (4×4) pixel array photoplethysmograph device 400, comprising sixteen pixels 401. It will be understood that the array can be considerably larger than this if required.

Each pixel 401 preferably comprises a photodetector, detector circuit, band pass filter, and demodulator. Such an apparatus provides sixteen simultaneous (parallel) plethysmograms, detected by light from tissue illuminating each pixel in the array. The array does not have to be square. For example, the array could comprise 4×16 pixels, or 1×256 pixels etc. Each pixel may respond to light from a common light source modulated with a common modulation frequency. Alternatively, each pixel could correspond to a respective independently driven light source, so that different modulation frequencies could be used for each pixel. Alternatively, each pixel could correspond to a respective light source with all light sources being driven using a common modulation signal.

An array of detectors opens up a whole new dimension of signal processing by using several parallel channels of the aforementioned processing. The pixel array enables the production of a spatial map of blood parameters (e.g. pulse rate, breathing rate and blood constituents) from the target object. Multiple channels may be processed in parallel thereby allowing an arbitration scheme to be employed to select the optimum SNR. Further the multiple channels can be processed by independent component analysis, principal component analysis or blind source separation for example, to extract the fundamental signal when buried within noise and other interfering signals. It is thereby possible to produce robust pulse and breathing rate measurements and spatial blood constituent measurements when more than one wavelength is used. Independent component analysis etc can also be used to reduce movement artefacts. Movement artefact is often a serious problem for photoplethysmograph systems: the problem and other methods of reduction have been described by Smith and Hayes (Matthew J. Hayes and Peter R. Smith, "*Artifact reduction in photoplethysmography*". Applied Optics, Vol. 37, No. 31, November 1998).

A signal processing means implemented on- or off-chip in an analogue or digital domain that analyses the plethysmogram from each pixel may be implemented to extract the breathing rate, pulse rate, blood constituents etc. In general both pre- and post-processing can be performed for each pixel thereby allowing full field, spatial signal processing algorithms to be used.

Non-Contact Photoplethysmography

The single wavelength photoplethysmograph devices, multiple wavelength photoplethysmograph devices, and pixel array photoplethysmograph devices described above can each be used in a non-contact reflection mode.

In photoplethysmography the photodetector 104 is in contact with the target object, e.g. the tissue surface. A large proportion of the light from the source 102 is reflected from the tissue surface, but because the photodetector 104 is in contact with the tissue, this surface reflected light is not detected. A small proportion of light penetrates and interacts with the tissue, and then emerges incident to the photodetector, where it is detected, amplified and processed, which gives rise to the plethysmogram signal.

In non-contact photoplethysmography the photodetector 104 is not in contact with the tissue. This results in detection of the greater proportion of light reflected at the tissue surface as well as light that has penetrated the tissue. The detected signal now comprises a much larger DC offset caused by the reflected light, onto which is superimposed a much smaller plethysmogram signal. The light reflected from the tissue surface has not interacted with blood and hence contains no information useful to the plethysmogram.

It will be appreciated that the DC offset caused by tissue surface reflections will reduce the dynamic range of the photoplethysmograph. Therefore it is of benefit to filter out reflected light when using a non-contact photoplethysmograph. This can be done by using a polarising filter.

A polarising filter selectively polarises or filters light polarised along a given axis. This polarity is retained when light is reflected but lost when light is scattered. If the light incident on the tissue is polarised, the light reflected at the surface retains this polarity and can be attenuated by a filter orientated with its polarity at 90 degrees to that of the incident light. However, light that penetrates the tissue and is scattered by the blood and other media loses its polarity and hence passes through the horizontal polarising filter, and is detected by the photodetector.

Figure 5A:
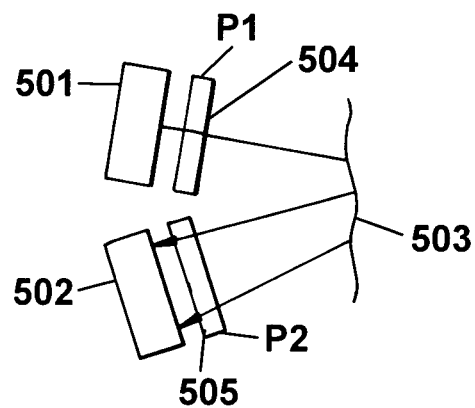
FIG. 5a is a schematic side view of a non-contact photoplethysmograph device with polarising filters.

With reference to FIG. 5, a first polarising filter 504 polarises light from a modulated light source 501 along a given polarisation axis P1. The polarised light is directed towards the target object 503, from which a proportion of the light is reflected from the surface and scattered from within the target object.

A second polarising filter 505 is disposed in front of the detector 502 that receives the light from the target object. The second polarising filter has a polarisation axis P2 and attenuates polarised light incident to the photodetector. The attenuation is at its greatest when the polarisation axis P2 of the second polarising filter 505 is at 90 degrees (orthogonal) to the axis of the polarised light. Thus, the first and second polarising filters 504, 505 are preferably arranged so that their respective polarisation axes P1, P2 are orthogonal to one another. In this way, the light reflected from the surface that retains its polarisation is substantially or completely attenuated, while the light that has been scattered from media within the target object and has lost its polarisation state has significantly reduced attenuation.

The devices described above can provide significant attenuation of narrow band interference that result from sources of ambient light (such as those produced by fluorescent lamps, computer monitors and incandescent light bulbs), electromagnetic interference, and noise spikes intrinsic to the apparatus and method of plethysmography, for example harmonics generated in analogue-to-digital converters. The modulation and demodulation frequencies may be selected to avoid harmonics of these interferences and, in conjunction with filtering, to attenuate broadband noise intrinsic to the device including white noise, flicker noise and shot noise.

In the arrangement of FIG. 2, it is not necessary to know or maintain the phase relationship between the modulating carrier and demodulating local oscillator, because the demodulation process is insensitive to the phase difference between the two. It is therefore not necessary to calibrate for or consider any constant phase delay in the detected signal caused by the signal conditioning circuitry or the propagation of light in tissue.

It will also be appreciated that the technical features can be embodied in various forms. For example, the driver circuit, light source, photodetector, detector, band pass filter and demodulation process can be implemented, where appropriate, as a digital signal processing algorithm, a custom analogue integrated circuit, discrete analogue electronic components or as a combination of analogue and digital signal processing functions.

A further modification would be to sample the output of the detector circuit and implement band pass filter, demodulator and signal processing on a digital signal processor or microprocessor as part of a signal processing algorithm.

A further modification would be to implement the photodetector, detector, band pass filter, demodulator and signal processor on a microchip as a VLSI mixed signal design.

Variants and Noise Management

A combination of some or all of each of these features can be utilised to produce the desired system such that the signal can be separated from the noise. However, careful design should be made at the delivery of the light source and the collection of the received light signal. For example the magnitude of the photoplethysmogram current detected in the total photocurrent is quite small and hence a poorly designed front end can result in a distorted or submerged signal in amongst the noise. The delivery of a pulsed voltage to the light source should be made by cabling that is shielded and does not run alongside the receiving photodiode connections. If this occurs then a displacement current may be induced in the photodetector equal to I=CdV/dt.

Depending upon the magnitude of the light source power, the detector size and the rate of change of voltage will establish the maximum value of the coupling capacitance allowed. It is good design practice to ensure that the induced displacement current is limited to no more than typically 1% of the detected current.

Other design criteria may be as follows:
a) The input bias current should be less than ~1% of the DC light level detected.
b) The voltage and current noise should be less than the shot noise set by the DC light level detected.
c) The choice of a transimpedance amplifier should be made such that its 1/f corner frequency is less than the modulating carrier frequency.
d) The carrier rise and fall time can be slewed to reduce the coupling.
e) Good PCB design practice can be observed to avoid the coupling of signals from high power noisy components to a sensitive sensor front end, particularly a transimpedance amplifier. Multilayer PCBs can be used to keep power supplies and ground returns as short as possible and therefore minimise ground bounce and other forms of noise coupling. Multilayer PCB design can be used for a reflectance probe to reduce the coupling of displacement currents from the light source voltage pulse to the receiving photo diode connection.

There now follows an example configuration. However, it should be noted that this is not the only configuration as combinations of some or all of these features can lead to a beneficial design.

EXAMPLE

Figure 6:
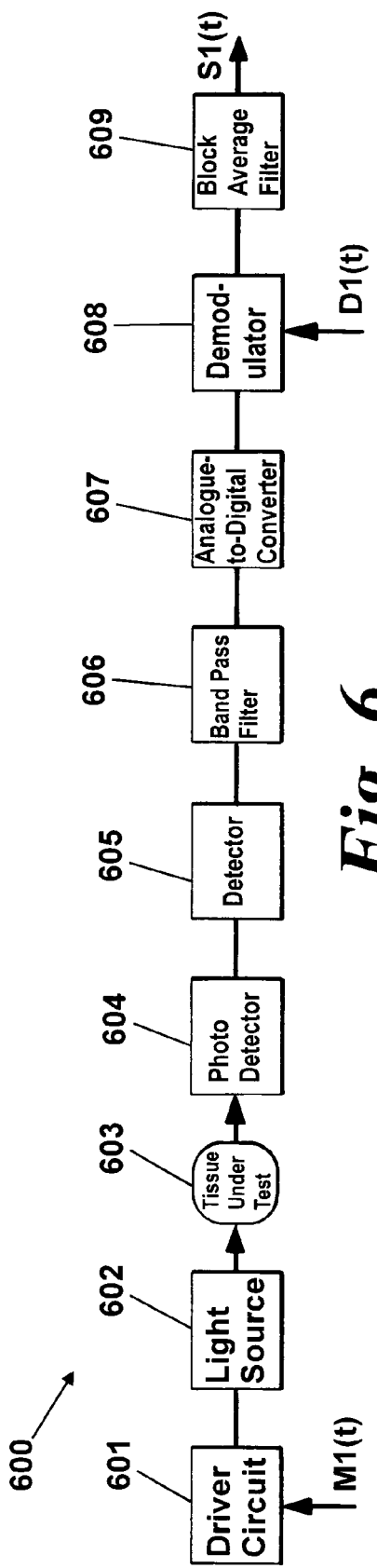
FIG. 6 is a functional block diagram of a single wavelength photoplethysmograph device.

FIG. 6 is a functional block diagram illustrating the architecture of a preferred plethysmography device 600 including a driver circuit 601 for driving a light source 602 with a modulated carrier signal such that the output intensity varies as a function of the modulation signal at a modulation frequency. The light source illuminates a target object 603 and light returned from the target object is received by photodetector 604 to generate an electrical signal as a function of the intensity of received light. Detector 605 converts the electrical current output of photodetector 604 to a voltage signal. This is filtered by bandpass filter 606 and converted to a digital signal in analogue to digital converter 607. A demodulator 608 (which may be of the type described in connection with FIG. 2) has a local oscillator signal D1(t) which is preferably substantially the same frequency as the modulation signal M1(t) of driver circuit 601. A block average filter 609 is used to produce an output plethysmogram S1(t).

Figure 5B:
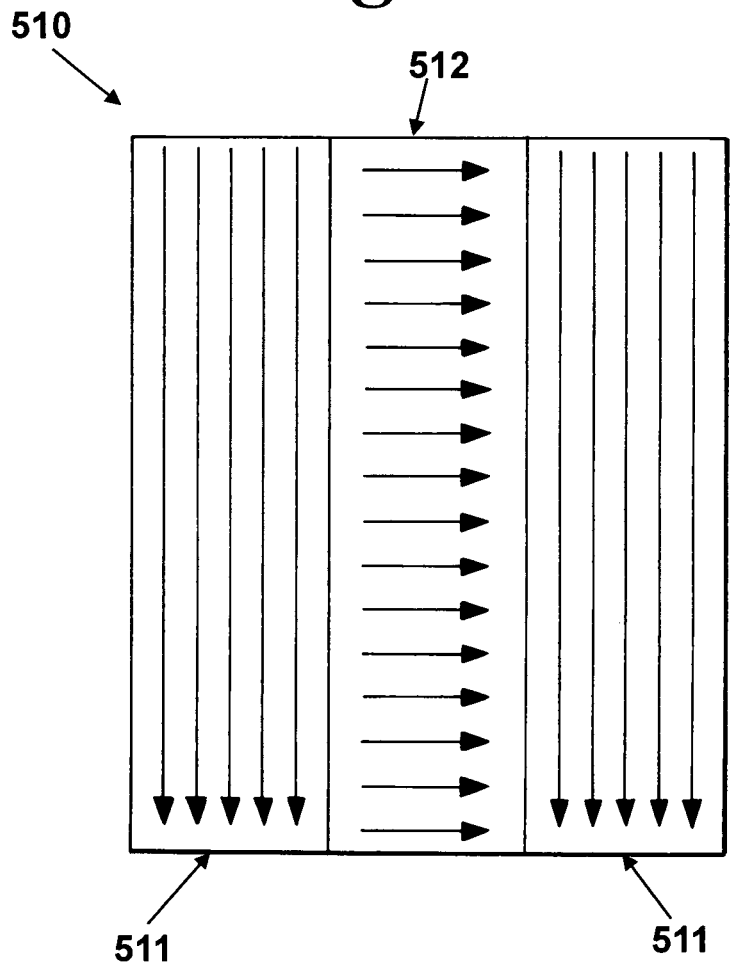
FIG. 5b is a plan view of a polarising filter for use with the reflectance mode photoplethysmograph device of FIG. 7.
Figure 7:
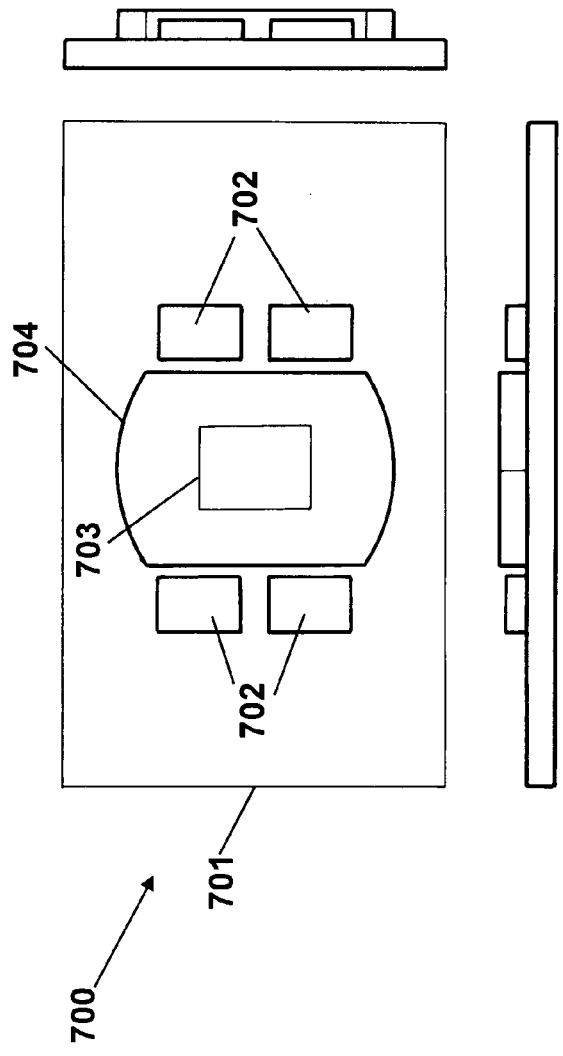
FIG. 7 is a schematic plan view, side view and end view of a reflectance mode photoplethysmograph device.

FIG. 7 illustrates a reflectance probe 700 providing the light source and photodetectors for the apparatus of FIG. 6. The reflectance probe 700 comprises four light emitting devices 702 for emitting modulated light signals of a single wavelength, in order to illuminate the tissue under test. A photodiode 704, which could be an array of detectors, has a given active area 703 which is used to detect the light reflected back from the tissue under test. A suitable polarising filter element 510 incorporating first and second crossed polarising filter elements 511 and 512 is shown in FIG. 5b. When the probe is used in non-contact mode, this element 510 is placed over the top of light emitting devices 702 and photodiode 704. In a general aspect, this arrangement provides active surfaces of a light source and detector directed towards substantially the same point on a surface of a target body.

The light emitting devices are preferably light emitting diodes (LEDs) with a peak spectral response between 400 nm and 600 nm. Generally, the wavelength is selected based on the optical characteristics of the tissue under investigation. This exemplary photoplethysmograph device 700 is particularly suited to the measurement of heart rate and breathing rate in humans, therefore the wavelengths are selected based on the optical properties of human tissue and blood which exhibit strong absorption characteristics between 400 nm and 600 nm. Studies were mainly carried out at the absorption spectrum between 500 nm and 600 nm. However a strong absorption spectrum also exists at 440 nm and a device operating around this wavelength would also produce favourable results. More specifically, there are three versions of the reflectance probe: one with LEDs that have a peak spectral response of 512 nm; one with LEDs that have a peak spectral response of 562 nm; one with LEDs that have a peak spectral response of 574 nm. These are the preferred wavelengths because they are commercially available and economical however others can be used if supply and economics permit. The range of wavelengths between 500 nm and 600 nm is particularly preferred since, although the signal may improve below 500 nm, the penetration depth of the light decreases which may, in some circumstances, result in insufficient light reaching the pulsatile blood in the skin's arterioles.

The LEDs and photodiode are mounted side by side on four-layer printed circuit board (PCB). The use of screened power and signal cables and multi-layer PCB design improves immunity to noise pickup and electrical cross talk. The height of the photodiode package is preferably greater than that of the LEDs to reduce direct coupling of light onto the active area (optical crosstalk). The lateral separation between the LEDs 702 and photodiode active area 703 increases the path length that the light must travel through the tissue which improves the signal.

Figure 10:
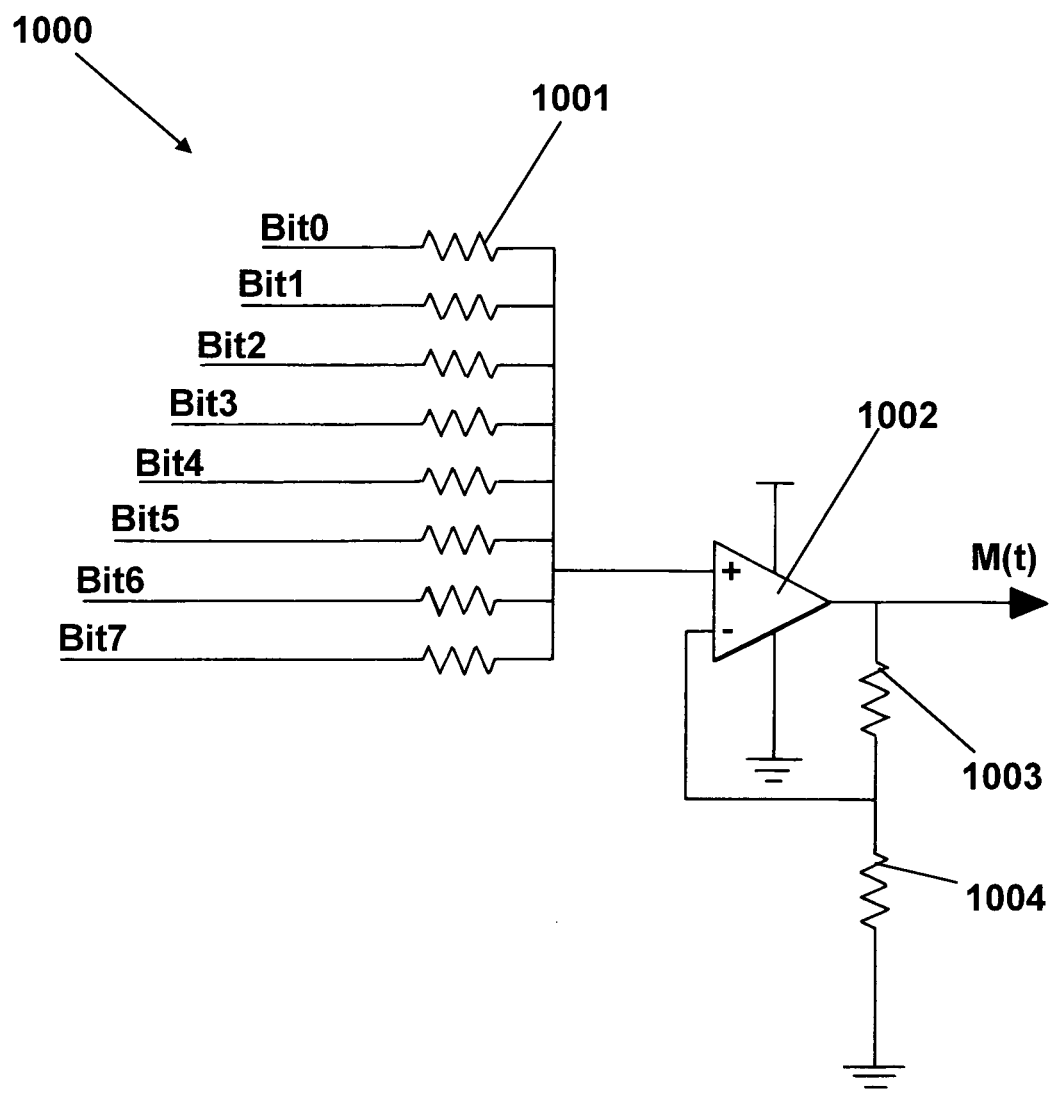
FIG. 10 is a circuit diagram of a light source driver circuit suitable for use in the photoplethysmograph devices described herein.

The light source is excited at a given frequency and amplitude by a modulating carrier from the driver circuit 601. The driver circuit 601 is a digital-to-analogue converter implemented using a current summing amplifier as shown in FIG. 10. An 8-bit DAC input signal is generated by a microcontroller and presents 255 discrete amplitude levels via resistors 1001. The carrier frequency is determined by the rate at which the input signal is clocked. The output signal M(t) is a square wave of a given carrier frequency with an amplitude that can be varied between 0 volts and the fall-scale output range of the op amp 1002. The closed loop voltage gain of the op amp 1002 is set by the inverting feedback fraction of resistors 1003 and 1004. This can be adjusted so that a digital input of 255 gives a full-scale analogue output.

Light incident to the photodiode 604 may be passed through a visible light optical filter that attenuates wavelengths above 600 nm. The filter may be incorporated into the photodiode and positioned in front of its active area. The peak spectral response of the photodiode is preferably between 500 nm and 600 nm. More specifically, the peak spectral response of the photodiode may be 580 nm. The light filter may roll off the photodiode response above 600 nm which serves to attenuate interference from light above this wavelength.

Figure 8:
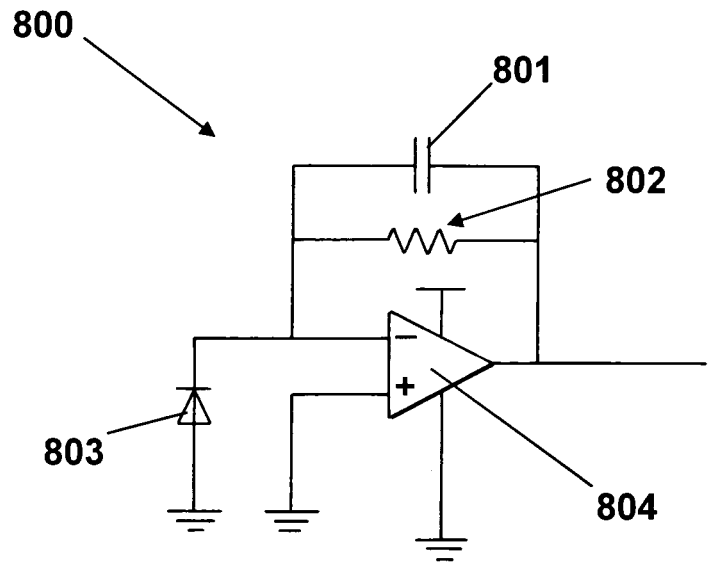
FIG. 8 is a circuit diagram of a transimpedance amplifier suitable for use in the photoplethysmograph devices described herein.

Light incident on the photodiode 604 generates an analogue current. The photodiode current is coupled to the current-to-voltage converter 605, which may be a transimpedance amplifier 800 as illustrated in FIG. 8. The transimpedance amplifier 800 is preferably designed so that its gain rolls off above the modulation frequency. This low pass filter response reduces noise and aliasing. The amplifier 800 is designed so that a feedback capacitor 801 is as near as possible to the value of the photodiode junction capacitance which reduces voltage noise gain. This must be balanced against the requirement for transimpedance roll-off and amplifier stability which is controlled by the feedback capacitor 801 and resistor 802.

Figure 9:
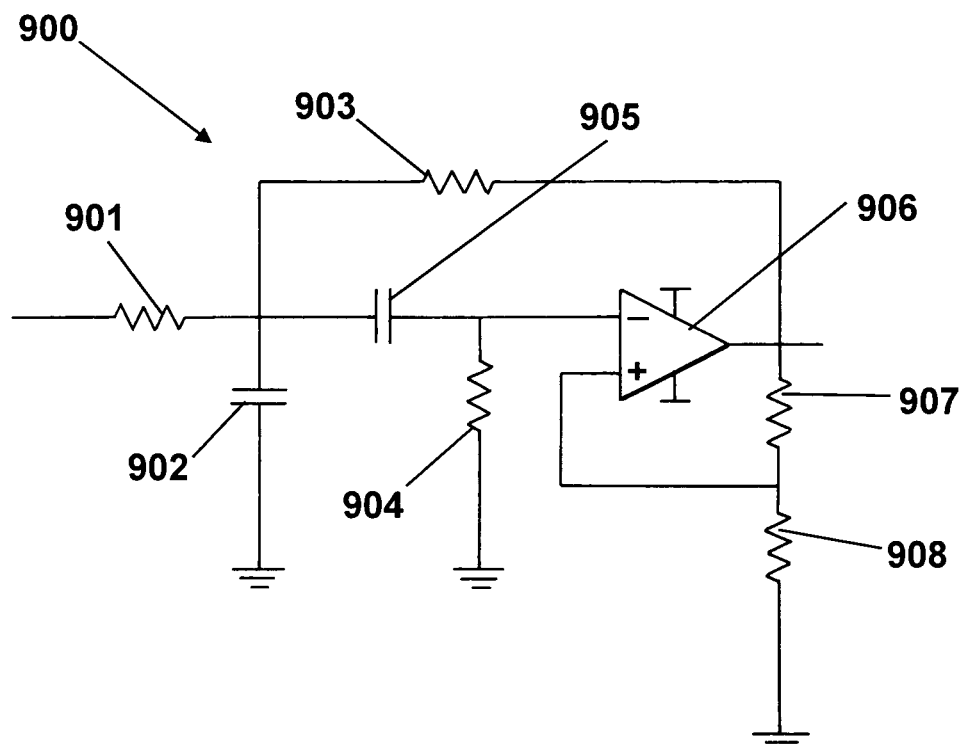
FIG. 9 is a circuit diagram of a band pass filter circuit suitable for use in the photoplethysmograph devices described herein.

The band pass filter 606 is preferably an active Sallen-Key type with an RC frequency response though it will be appreciated that Chebychev, Butterworth and other responses could be used. An exemplary filter 900 is shown in more detail in FIG. 9. Though the filter 900 is designed using an operational amplifier 906, it will be appreciated that a band pass filter frequency response can be produced by other methods. The filter 900 is designed to have a centre frequency as close as possible to the modulating frequency which, in this example, is 570 Hz, and low tolerance components are selected to help achieve this. The inverting input feedback network 907 and 908 of the operational amplifier sets the filter gain and bandwidth. This is preferably designed to give as narrow as possible bandwidth while not making the filter centre frequency overly sensitive to tolerance of components 901, 902, 903, 904 and 905. The high pass roll-off of the filter attenuates noise below the modulation frequency and the low pass roll-off attenuates noise above the modulation frequency, which also provides anti-alias filtering. It will be appreciated that although the band pass filter response is in this example implemented as a single band pass filter, it could also be implemented with separate high and low pass filters of single or multiple stages.

The output of the band pass filter is an analogue voltage that represents the carrier-modulated plethysmogram. As the detected carrier modulated plethysmogram has been band pass filtered and its high and low frequency content therefore attenuated, the output signal of the filter is a sine wave with a frequency equal to that of the fundamental frequency of the modulating carriers.

The plethysmogram is recovered by demodulating the band pass filtered, carrier modulated plethysmogram signal. Demodulation and further signal conditioning may be performed using digital signal processing. However, all of this processing can be carried out in the analogue domain using circuits such as a Gilbert cell I and Q mixer and a low pass filter for each channel forming a two-channel lock-in. Therefore an analogue-to-digital converter 607 follows the band pass filter and is used to sample the analogue voltage at the filter 606 output. It should be noted that the filter is preferably the last stage before the analogue-to-digital converter 607. This ensures the converter 607 is presented with band pass filtered noise and not broadband white noise and flicker noise which would be present at the output of any active circuit stage without a limited frequency response. It will be understood by those skilled in the art that this will reduce the level of noise appearing at the output of the demodulator 608.

For analogue to digital conversion and subsequent demodulation, the sample rate should preferably be at least four times a multiple integer of the modulation frequency. For example, the sample rate should be 4, 8 12, 16 and so forth times the modulation frequency. In a preferred arrangement, the modulation frequency is 570 Hz and the sample frequency is 4560 Hz: sample frequency is 8 times (2×4) the modulating carrier frequency.

Sample Frequency=$n$*4*Modulation Frequency
(where $n$ is an integer)

Minimum Sample Frequency=4*Modulation Frequency.

Figure 11:
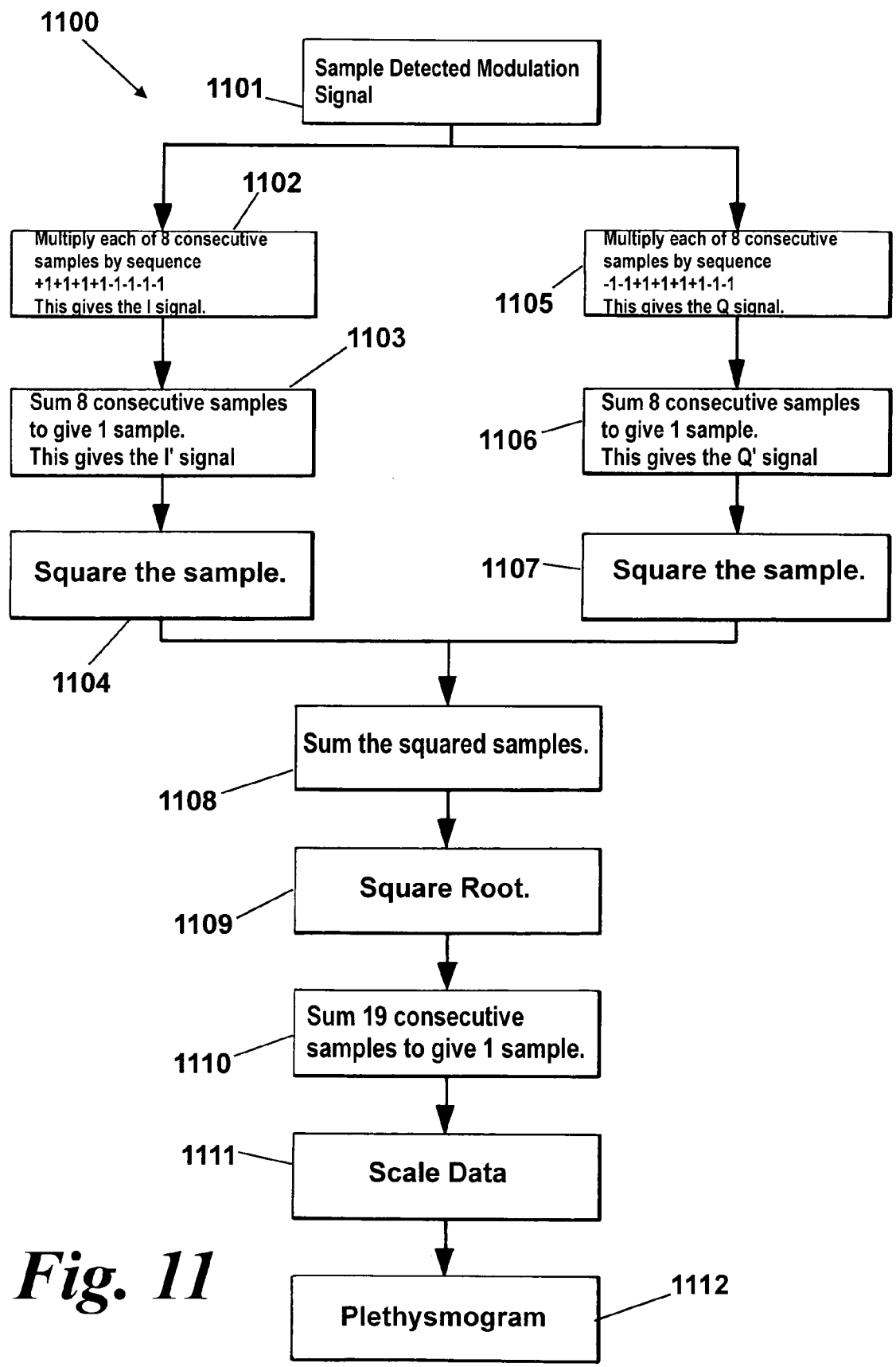
FIG. 11 is a process flow diagram illustrating a demodulation algorithm suitable for use in the photoplethysmograph devices described herein.

FIG. 11 shows a flow chart of an exemplary demodulator algorithm as carried out in the demodulator of FIG. 2. As previously described, the demodulator comprises a multiplexer for splitting the modulated signal into two channels to give a first modulated input signal and a second modulated input signal.

Considering the first modulated signal, this is multiplied with a first demodulator carrier. The demodulator local oscillator (LO) is a square wave with an amplitude of 1, a peak-to-peak amplitude of 2, and therefore sample values of +1 and −1. Its duty cycle is 50%. Its frequency is equal to the modulating carrier frequency. In this example the modulation, and therefore demodulation frequency, is 570 Hz, and the sample rate is 4560 Hz. Therefore, the demodulation waveform comprises eight samples: four of the value +1 corresponding to the positive cycle of the carrier, and four of the value −1 corresponding with the negative cycle of the carrier. Therefore one cycle of the demodulating LO is represented by the samples +1, +1, +1, +1, −1, −1, −1, −1 and this pattern is repeated, ad-infinitum, to generate a continuous digital signal. To multiply the first modulated signal with the first demodulator LO and therefore obtain the I signal (step 1102), each measured value of the modulated signal is multiplied with a corresponding-in-time value of the demodulator local oscillator signal: the modulated signal is multiplied by either +1 or −1. The use of multiplication by +1 and −1 is such that the processing is relatively simple on chip and such an approach is easily transferred to a single integrated circuit if required.

Now considering the second modulated signal, this is multiplied with a second demodulator LO. The demodulator LO is a square wave with an amplitude of 1, a peak-to-peak amplitude of 2, and therefore sample values of +1 and −1. Its duty cycle is 50%. Its frequency is equal to the modulation carrier frequency. In this example the modulation, and therefore demodulation frequency, is 570 Hz and the sample rate is 4560 Hz. Therefore, the demodulation waveform consists of eight samples: four of the value +1 corresponding to the positive cycle of the carrier, and four of the value −1 corresponding with the negative cycle of the carrier. However, the second demodulator carrier is phase shifted by 90 degrees with respect to the first demodulator carrier. Therefore one cycle of the demodulation carrier is represented by the samples −1, −1, +1, +1, +1, +1, −1, −1 and this pattern is repeated, ad-infinitum, to generate a continuous demodulation LO. Note that this is not the same as the first demodulated carrier signal given above but is a 90 degree phase shifted version of it. To multiply the first modulated signal with the first demodulator LO and therefore obtain the Q signal, each measured value of the modulated signal is multiplied (step 1105) with a corresponding-in-time value of the demodulated carrier signal: it was multiplied by either +1 or −1.

It will now be appreciated that, in this example which uses an analogue-to-digital converter and digital demodulator, the requirement for sampling the band pass filtered detected signal, at a minimum of four times the modulation frequency or at a integer multiple of four times the modulation frequency is so that the 90 degree phase shift can be accurately implemented, by shifting the sampled demodulation LO one-quarter of its cycle.

Separately, the I and Q signals are each low pass filtered to remove unwanted harmonics and products of the multiplication process, and decimated to reduced the sample rate. This is carried out by summing each signal in eight-sample-long blocks (steps 1103 and 1106). For each channel, the first eight samples are summed then the second eight and so forth ad infinitum. It will be understood that this is equivalent to integrating the I and Q signal over one cycle. It will be appreciated that this is an averaging process, which gives a low pass filter frequency response and therefore attenuates the high frequency multiplier products. It will also be appreciated that this is an average filter that gives a frequency response with large nulls at multiples of the carrier frequency. This provides good attenuation of modulation carrier harmonics. Finally it will be appreciated that in summing eight samples to one sample, the process also acts as a decimation stage. This reduced sample rate eases computational complexity of later signal processing stages and reduces the analogue-to-digital converter noise floor improving signal-to-noise ratio.

The filtered and decimated I signal is now called I'. The filtered and decimated Q signal is now called Q'.

Finally, the I' and Q' signals are demultiplexed back into one signal: the demodulated plethysmogram. Each I' sample is multiplied by itself to give $I'^2$ (step 1104). Each Q' sample is multiplied with itself to give $Q'^2$ (step 1107). Each $I'^2$ sample is summed with its corresponding $Q'^2$ sample to give: $I'^2+Q'^2$ (step 1108). Each summed sample is square rooted: $(I'^2+Q'^2)^{0.5}$ (step 1109) to give a plethysmogram sample.

The final stage in the exemplary photoplethysmograph device 600 is the block average filter 609. The block average filter sums consecutive blocks of 19 samples (step 1110) to give one sample. This provides the function of an averaging filter and decimator and its characteristics are used to attenuate harmonically related noise, in particular the noise generated by 60 Hz computer monitors. The averaging filter has a frequency response that gives a null (large attenuation) at multiples of the sampling frequency. The original sampling frequency of 4560 Hz has been decimated by 8, then by 19, giving a final sample frequency of 30 Hz. Therefore the averaging filter response gives large attenuation at multiples of 30 Hz.

The light source 602 is modulated with a 570 Hz carrier. This positions it halfway between 540 Hz (9th harmonic of 60 Hz), and 600 Hz (10th harmonic of 60 Hz). At the output of the demodulator, these harmonics appear at 30 Hz (with all other harmonics appearing at even multiples of 30 Hz). The block average filter 609 is a simple method to attenuate this interference. The output of this final stage of filtering (steps 1111, 1112) is the plethysmogram (S1($t$)).

It will be appreciated that the final sample rate, and therefore the frequency characteristics of the final stage block average filter, will depend on the decimator ratios used in the demodulator 608 and block average filter 609. Therefore, these ratios can be adjusted to give attenuation of different harmonics by the block average filter. A range of values for modulation carrier frequency, sample rate and decimation ratios are given in Table 1 below. A modulation carrier frequency, sample rate and decimation ratio is chosen to attenuate a given, problematic, refresh rate.

| Refresh Rate (Hz) | Refresh Rate Harmonic (Hz) | Refresh Rate Harmonic (Hz) | Modulation Carrier Frequency (Hz) | Harmonic after Demodulation (Hz) | Sample Rate (8 × Carrier) (Hz) | Decimation Ratio |
|---|---|---|---|---|---|---|
| 60 | 540 | 600 | 570 | 30 | 4560 | 152 |
| 70 | 490 | 560 | 525 | 35 | 4200 | 120 |
| 72 | 504 | 576 | 540 | 36 | 4320 | 120 |
| 75 | 525 | 600 | 562.5 | 37.5 | 4500 | 120 |
| 85 | 510 | 595 | 552.5 | 42.5 | 4420 | 104 |

A typical output signal can be seen in FIG. 13. FIG. 13a shows the combined AC and DC components. FIG. 13b shows the magnified AC components. The higher frequency periodicity is the measured subject's pulse rate. The lower frequency periodicity is the measured subject's breathing rate, which was verified with a thermistor probe. Algorithms for determining the pulse rate are commonly found in the literature and consist of peak detection etc.

Applications

An advantage of the plethysmograph devices described here is that a reliable reflectance mode sensor can be used on many sites of the body not previously suitable for photoplethysmogram sensing. For example, the forehead is a highly convenient site for monitoring in harsh conditions such as employees working in the mining or chemical processing industry who have to wear safety helmets. The device can be conveniently located in the band of the safety helmet or on the wrist under a watch or other such convenient places on the body. Forehead sensors and head placement has been described in Branche et al: "*Measurement Reproducibility and Sensor Placement Considerations in Designing a Wearable Pulse Oximeter for Military Applications*", IEEE 30th Annual Northeast Bioengineering Conference, Springfield, Mass., United States, 2004. Their paper reported a hat mounted forehead sensor for military applications.

Another harsh environment is in the maternity suite in hospitals for newborns that need resuscitating. Placing such a transducer on the forehead allows the medic to concentrate on the neo-natal care whilst continually hearing an audible bleep indicating the pulse rate. Such a device will be highly suitable for other harsh and routine environments in the health and safety fields. On the other hand soft applications exist again for mounting in clothing for social, domestic, sports and biometric applications.

Results

FIGS. 13, 14 and 15 show results from experiments with the exemplary photoplethysmograph devices previously described. The photoplethysmograph was used to record the plethysmogram by illuminating the subject's forehead. Therefore these graphs show the forehead plethysmogram.

FIG. 13a shows the plethysmogram AC and DC component. This is a traditional plethysmogram signal that would be expected. FIG. 13b shows the AC component which has been magnified. The pulsatile signal caused by the arterial pulse travelling under the sensor is clearly visible. This is superimposed on another, lower frequency, signal which has a period of approximately 10 seconds. This is the breathing signal caused by variations in blood volume as the subject inhales and exhales. In this experiment the subject breathed at a fairly constant rate and depth, inhaling and exhaling once every 8 seconds. This is clearly seen between 10 and 60 seconds.

Figure 14A:
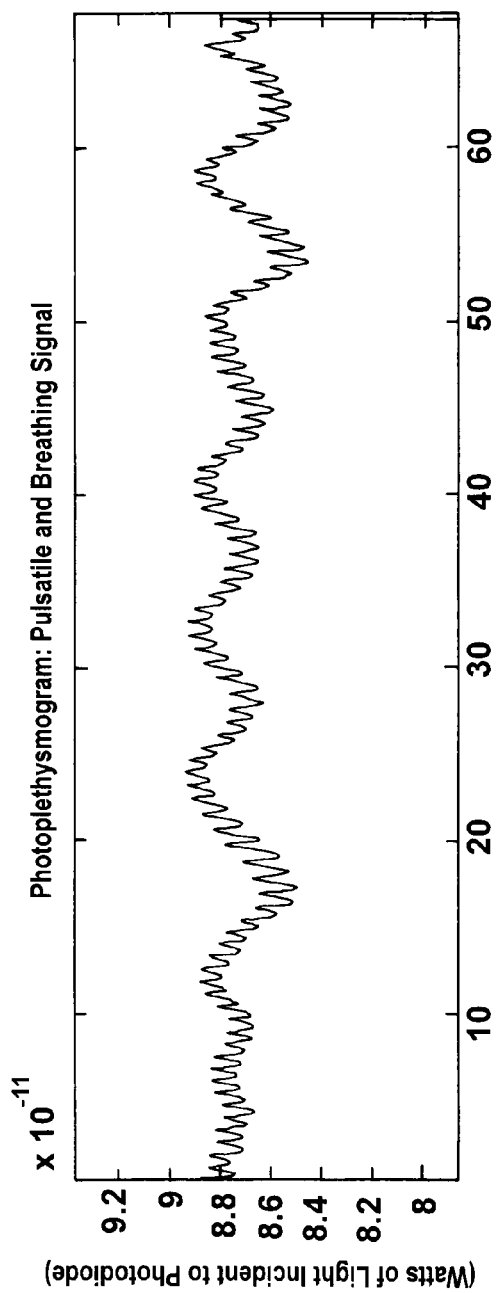
FIG. 14a is a photoplethysmogram showing combined pulsatile and breathing signal.
Figure 14B:
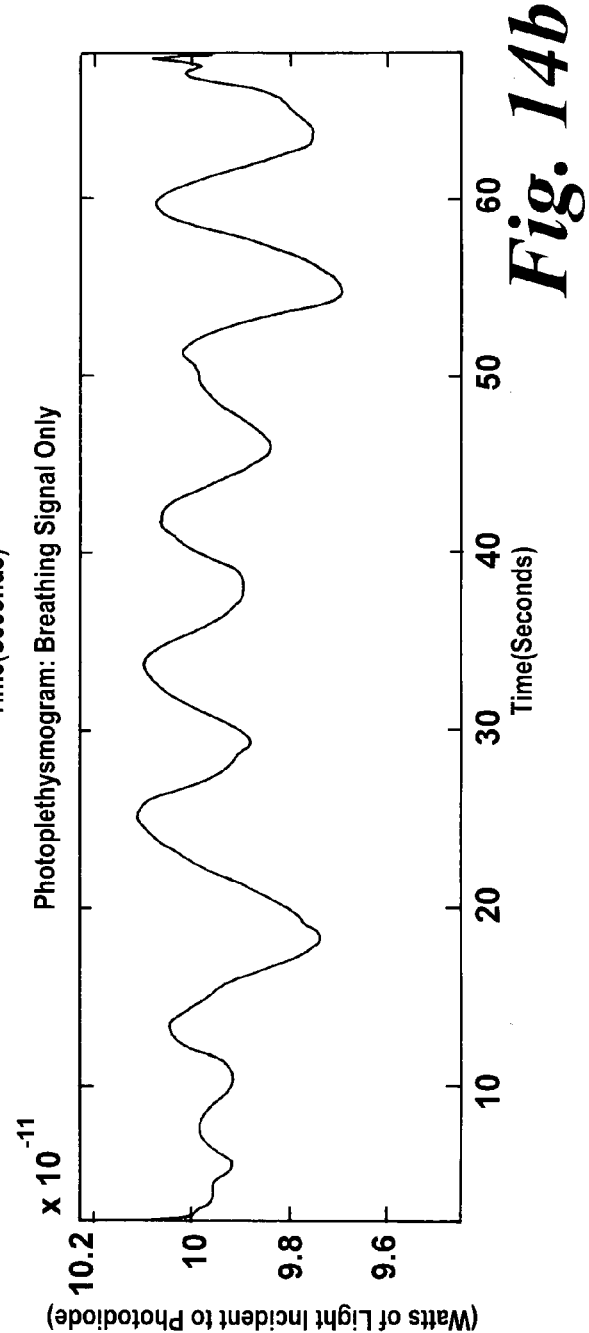
FIG. 14b is a photoplethysmogram showing the breathing signal of FIG. 14a only.

FIG. 14a shows a magnified plethysmogram AC component. FIG. 14b shows the AC component after it has been band pass filtered to attenuate the pulsatile signal. The photoplethysmogram breathing signal is clearly visible.

Figure 15A:
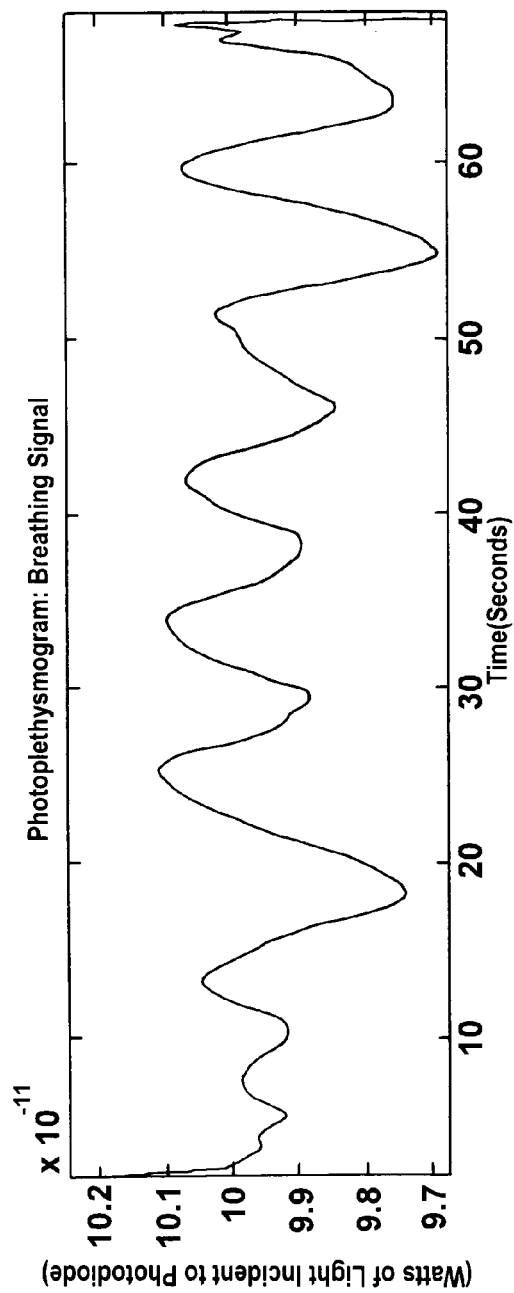
FIG. 15a is a photoplethysmogram showing a breathing signal only.
Figure 15B:
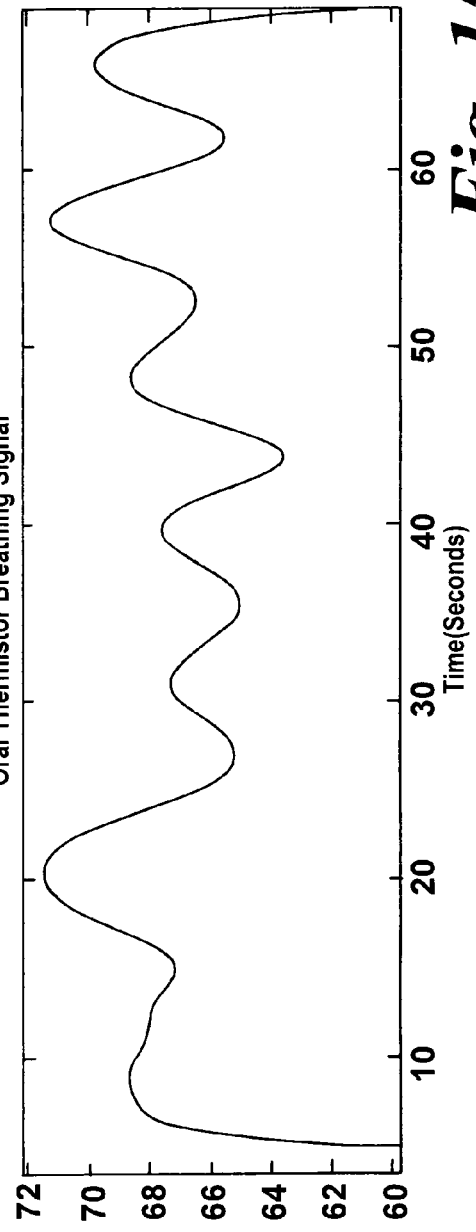
FIG. 15b is a corresponding breathing signal as measured by an oral thermistor.

FIG. 15 confirms that this low frequency AC signal is the photoplethysmogram breathing signal. FIG. 15a shows the photoplethysmogram breathing signal. FIG. 15b shows the signal from an oral thermistor. This thermistor was placed in a plastic tube through which the subject breathed. As the subject exhales, air from the lungs warmed by the body causes a rise in temperature. As the subject inhales, cooler air from the room is drawn across the thermistor and the sensor records a drop in temperature. Thus breathing rate can be measured and correlated with the photoplethysmogram signal to validate the photoplethysmogram breathing rate signal.

Inspection and comparison of FIGS. 15a and 15b show that the plethysmogram AC component contains both pulsatile and breathing information and that the exemplary photoplethysmograph detects these signals with ease. The two signals should be 180 degrees out of phase, which is the case. The small phase delay is caused by thermal capacitance of the thermistor.

In a general aspect, the demodulator outputs of the photoplethysmograph devices as described herein (e.g. plethysmogram $S1(t)$) generally provide a signal that is indicative of blood volume as a function of time. This can be analysed using techniques known to the skilled person. The output can also be used to deduce blood constituents or blood composition. The periodic rise and fall in detected light intensity is assumed to be solely due to the influx of arterial blood into the tissue. By using the peak and trough measurements, the attenuation due to the arterial blood can be measured. If this is performed at two different optical wavelengths, then the oxygen saturation (the ratio of oxygenated to deoxygenated blood) can be estimated, using known techniques.

Green Light Photoplethysmography

The technique of photoplethysmography is used in pulse oximeters which determine the relative oxygen saturation of blood. These devices are normally used in transmission mode: light is used to illuminate an area of tissue and the emergent light on the other side of the tissue is detected and processed to determine the percentage saturation. This technique is restricted to areas of skin thin enough for light to pass through, such as the fingers, toes and ear lobes.

The choice of light wavelength in transmission mode pulse oximetry is important. The absorption of light by blood decreases by an order of magnitude from 450 nm to 600 nm, then again from 600 nm to 650 nm and beyond. This absorption is a function of the photon path length and absorption coefficient and is very large in transmission mode. The result of this is that the attenuation of light between 450 nm and 600 nm is very high, to such an extent that very little light of wavelength below 600 nm will pass through an appendage such as the finger, toe or earlobe. Generally light is used at 650 nm or higher.

Similarly, much of the research of photoplethysmography has been with devices that work in the transmission mode, and hence light of a wavelength greater than 600 nm has been used.

When used in reflection mode the path length, and therefore overall absorption, is smaller. This is because the light does not pass through an appendage, but is scattered (or reflected) from the surface layers of tissue back to the detector. This means that light of between 450 nm and 600 nm can be used. However, the intensity is still very low and low noise detection techniques are necessary to achieve an adequate signal-to-noise ratio.

The advantage of using light of a wavelength that is strongly absorbed is because the main absorbing medium is blood. This means that a change in blood volume will cause a corresponding but larger change in the intensity of light between 450 nm and 600 nm than 600 nm and beyond. Hence, the light amplitude is modulated by the blood to a greater degree and therefore the pulsatile component of a reflectance photoplethysmogram signal is much larger when light between 450 nm and 600 nm is used than when light above 600 nm is used. This is illustrated by FIGS. 16 and 17.

Figure 16:
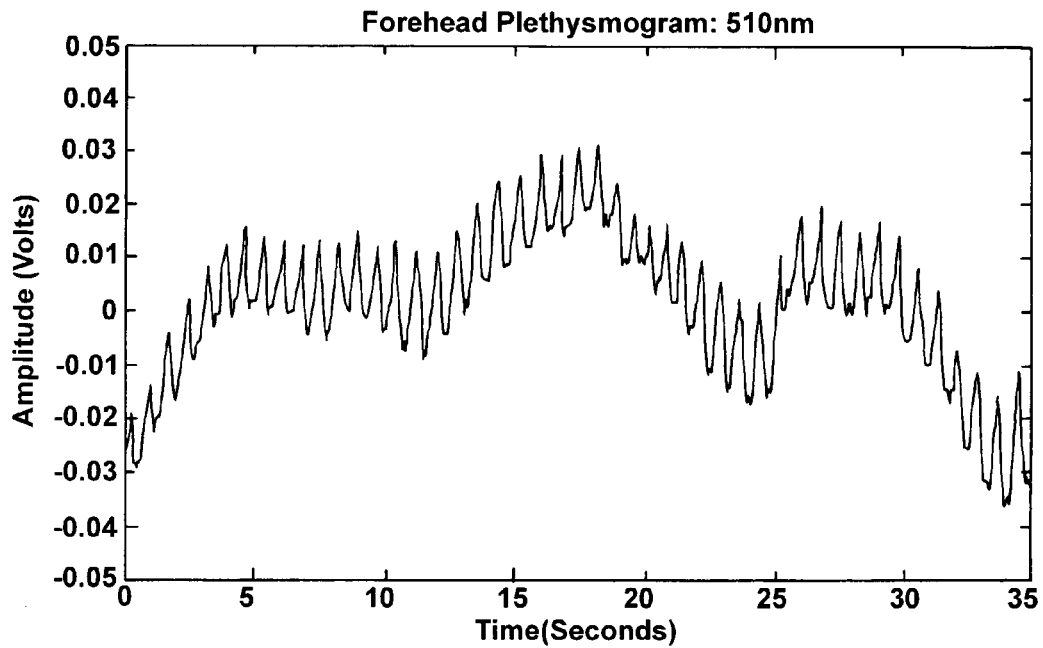
FIG. 16 is a photoplethysmogram recorded using a green light source of wavelength 510 nm.
Figure 17:
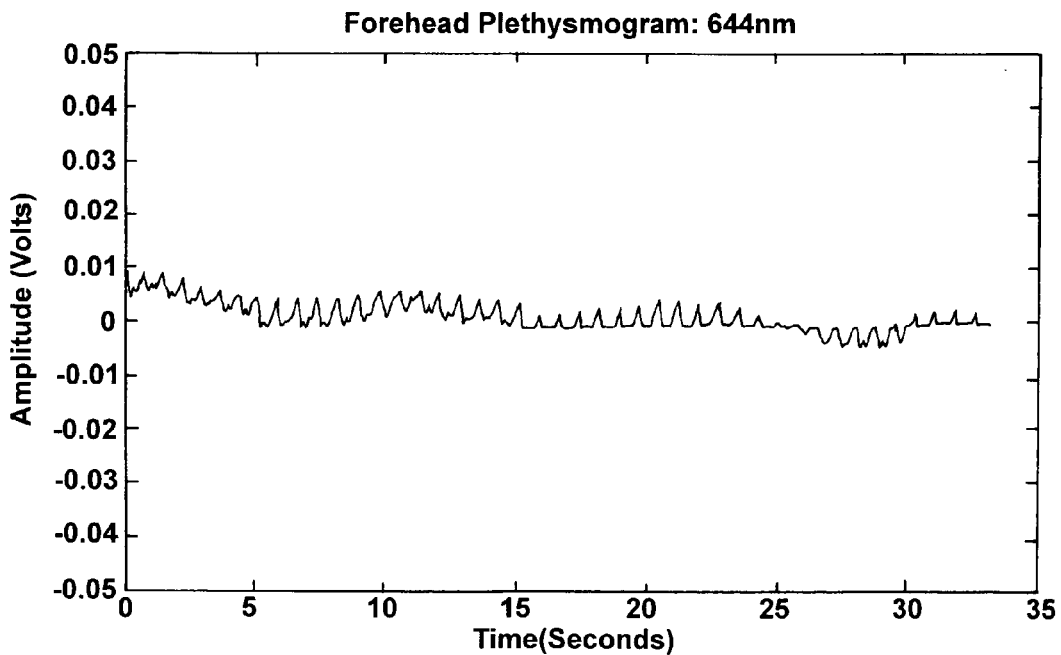
FIG. 17 is a photoplethysmogram recorded using a red light source of wavelength 644 nm.

FIG. 16 shows a photoplethysmogram using green light at a wavelength of 510 nm and FIG. 17 shows a photoplethysmogram using red light at a wavelength of 644 nm. The scaling of the y-axis in both plots is identical. It can be clearly seen that green light gives a larger pulsatile signal than red light. The pulse caused by the heart beat is clearly visible and of greater amplitude than when red light is used, with a corresponding improvement in signal-to-noise ratio.

Additionally, the results from the green light clearly show the breathing signal as a low frequency base line drift. The breathing signal was not easily observed when red light was used.

A number of the features described here can readily be used in conjunction with one another.

The use of modulated light with quadrature demodulation as described in connection with FIG. 2, in which the demodulator is insensitive to any phase difference between the modulation signal and the oscillator of the demodulator offers several advantages over prior art methods. The modulated photoplethysmogram signal can be band pass filtered at the modulating frequency to give good attenuation of DC ambient light, 100 Hz fluorescent light and 60 Hz computer monitor light, and flicker noise. It therefore gives better rejection to interference than prior art schemes that use DC (unmodulated) light, or modulated light with timeslot detection which is commonly used in pulse oximeters where it is used as a method of time division multiplexing between a red and an infra-red LED.

Quadrature demodulation is also insensitive to the difference between the phase of the modulating and demodulating carrier. This can simplify demodulation process to a simple algorithm, with no synchronisation of the carriers necessary.

Quadrature demodulation can readily be used in conjunction with the multiple wavelength plethysmograph devices described here, as well as with the pixel array devices, reflection mode devices and green light devices.

The combination of green light photoplethysmography and quadrature demodulation is found to be particularly advantageous. The use of green light maximises the amplitude of the detected photoplethysmogram signal and modulated light with a band pass filter and quadrature demodulation minimises the effects of noise. This combination thus maximises the signal-to-noise ratio and this means the heart rate and breathing rate can be extracted with greater reliability. In the case of heart rate detection it will reduce false positives or missed beats. In the case of the breathing signal it has clearly recovered a signal that has previously been difficult to detect, and the technique reduces the number of false positives and missed breaths.

The improved signal-to-noise ratio of the photoplethysmogram signal thus improves the detection of the features in the signal that relate to heart beat and breathing, and therefore improves the reliability of any algorithm that uses these features to determine the heart and breathing rate.

In various figures, such as FIGS. 1-3, 6, 12 and 18-20, the modulating signals are labelled M1(*t*) and the demodulating signals as D1(*t*) indicative of a signal in the continuous time domain i.e. an analogue signal with an amplitude that varies as a function of time. It will be understood that the arrangements described could readily be implemented using a digital signal processing algorithm, e.g. in a microprocessor. In such cases, it will be understood that M1, D1 would be discrete sampled signals, M1(*n*) and D1(*n*). Similarly, in FIG. 12 functional blocks G(s) and B(s) could be represented by signal conditioning algorithms B(z) 1201 and G(z) 1203.

Other embodiments are intentionally within the scope of the accompanying claims.

The invention claimed is:

1. A photoplethysmograph device comprising:
   a first light source for illuminating a target object;
   a modulator for driving the first light source such that an output intensity varies as a function of a modulation signal at a modulation frequency;
   a detector for receiving light from the target object and generating an electrical output as a function of intensity of the received light; and
   a demodulator for receiving the detector output, having at least one local oscillator and a demodulated output representative of the modulation signal and any sidebands thereof, in which the demodulator is insensitive to any phase difference between the modulation signal and the local oscillator, the demodulator is configured to:
      multiply the detector output with a first and second square wave output from the at least one local oscillator to produce an I signal and Q signal respectively; and
      to filter and decimate the I signal and Q signal by summing samples in blocks corresponding with a cycle of an oscillator frequency to produce a filtered and decimated I' signal and Q' signal, and to form the demodulated output by de-multiplexing the I' signal and Q' signal together,
   wherein the demodulated output is a signal indicative of blood volume as a function of time and/or blood composition,
   wherein the demodulator is a digital signal processing demodulator, and the at least one local oscillator is operable to produce the first square wave output at the oscillator frequency and at a first phase angle, and the second square wave output at the oscillator frequency and at a second phase angle, the second phase angle being at 90 degrees to the first phase angle.

2. The photoplethysmograph device of claim 1, wherein the oscillator frequency is substantially equal to the modulation frequency.

3. The photoplethysmograph device of claim 1 further including a feedback circuit adapted to adjust output intensity of the first light source as a function of the detector output or the demodulated output, and/or to maintain the output intensity of the light source at a level adequate to maintain detection of a plethysmogram from the demodulated output.

4. The photoplethysmograph device of claim 1, wherein the light source has an output in a range of an optical spectrum between 450 nm and 600 nm.

5. The photoplethysmograph device of claim 1 further comprising:
   a second light source for illuminating the target object with light of a different wavelength than the first light source,
   a second modulator for driving the second light source such that output intensity varies as a function of a second modulation signal, and
   a second demodulator for producing a second demodulated output representative of the second modulation signal.

6. The photoplethysmograph device of claim 5 in which the second demodulator is insensitive to any phase difference between the modulation signal and a local oscillator of the second demodulator.

7. The photoplethysmograph device of claim 5 further including means for generating, from the second demodulator output, a signal indicative of blood volume as a function of time and/or blood composition.

8. The photoplethysmograph device of claim 1 further including a band pass filter coupled between the detector output and an demodulator input having a pass band only sufficiently wide to pass the modulation frequency and any sidebands caused by plethysmogram amplitude modulation in the detector output.

9. The photoplethysmograph device of claim 8 in which the pass band is limited substantially to 25 Hz either side of the modulation frequency or a block averaging frequency is selected to reject noise sources with a frequency of 60 Hz.

10. The photoplethysmograph device of claim 1, wherein the
    at least one local oscillator comprises a first local oscillator producing the first square wave output, and
    a second local oscillator producing the second square wave output.

11. The photoplethysmograph device of claim 1 wherein the light source comprises four light emitting diodes, arranged around the detector, with two light emitting diodes arranged adjacent to each of two opposite edges of the detector.

12. The photoplethysmograph device of claim 1, further comprising a probe, the probe comprising the light source and detector, and the probe being located under a watch or mounted in clothing.

13. The photoplethysmograph device of claim 1, wherein the detector is positioned at a height greater than that of the first light source so as to reduce direct coupling of light onto an active surface of the detector.

14. The photoplethysmograph device of claim 1, wherein the light source comprises an active surface that emits light, and the light source and detector are disposed laterally adjacent to one another on a substrate such that the respective active surfaces of the light source and detector can be directed towards a same point on a surface of the target object.

15. A method of generating a plethysmogram comprising the steps of:
    illuminating a target object with a light source;
    driving the light source with a modulator such that an output intensity varies as a function of a modulation signal at a modulation frequency;
    receiving light from the target object with a detector and generating an electrical output as a function of intensity of the received light;
    receiving detector output in a demodulator having a local oscillator and producing a demodulated output representative of the modulation signal and any sidebands thereof, in which the demodulator is insensitive to any phase difference between the modulation signal and the oscillator of the demodulator, the demodulator is a digital signal processing demodulator comprising:

a first local oscillator producing a square wave output at an oscillator frequency and at a first phase angle, and a second local oscillator producing a square wave output at the oscillator frequency and at a second phase angle, the second phase angle being at 90 degrees to the first phase angle; and generating, from the demodulated output, a signal indicative of blood volume as a function of time and/or blood composition;

wherein the demodulator is configured to multiply the detector output with the output from the first and second local oscillator to produce an I signal and Q signal respectively, wherein the I signal and Q signal are filtered and decimated by summing samples in blocks corresponding with a cycle of the oscillator frequency to produce a filtered and decimated I' signal and Q' signal, the I' signal and Q' signal being demultiplexed together to form the demodulated output.

* * * * *